United States Patent
Meyer et al.

(10) Patent No.: US 10,779,718 B2
(45) Date of Patent: Sep. 22, 2020

(54) CHEEK RETRACTOR AND MOBILE DEVICE HOLDER

(71) Applicant: Align Technology, Inc., San Jose, CA (US)

(72) Inventors: Eric P. Meyer, Pleasanton, CA (US); Roman A. Roschin, Moscow (RU); Tzishing Jesse Lim, Mountain View, CA (US); Palak Mittal, Sunnyvale, CA (US); Stephan Albert Alexandre Dumothier, Houston, TX (US); Norman C. Su, San Jose, CA (US); Huameng Ivan Chu, San Mateo, CA (US)

(73) Assignee: Align Technology, Inc., San Jose, CA (US)

( * ) Notice: Subject to any disclaimer, the term of this patent is extended or adjusted under 35 U.S.C. 154(b) by 335 days.

(21) Appl. No.: 15/895,754

(22) Filed: Feb. 13, 2018

(65) Prior Publication Data

US 2018/0228359 A1    Aug. 16, 2018

Related U.S. Application Data

(60) Provisional application No. 62/458,477, filed on Feb. 13, 2017.

(51) Int. Cl.
*A61B 1/24* (2006.01)
*A61C 19/04* (2006.01)
(Continued)

(52) U.S. Cl.
CPC ............ *A61B 1/24* (2013.01); *A61B 1/00009* (2013.01); *A61C 5/90* (2017.02); *A61C 9/0093* (2013.01);
(Continued)

(58) Field of Classification Search
CPC ......... A61C 13/34; A61C 9/0053; A61C 5/90; G06T 7/70; G06T 7/60;
(Continued)

(56) References Cited

U.S. PATENT DOCUMENTS 2,171,695 A    9/1939   Harper
2,194,790 A    3/1940   Gluck
(Continued)

FOREIGN PATENT DOCUMENTS

AU       517102 B    11/1977
AU      3031677 A    11/1977
(Continued)

OTHER PUBLICATIONS

US 8,553,966 B1, 10/2013, Alpern et al. (withdrawn)
(Continued)

*Primary Examiner* — Matthew M Nelson
(74) *Attorney, Agent, or Firm* — Shay Glenn LLP

(57) ABSTRACT

The present disclosure provides methods, computing device readable medium, devices, and systems that utilize a cheek retractor and/or a mobile device holder for case assessment and/or dental treatments. One cheek retractor includes a first and a second lip holder, both including imaging markers of a predetermined size to determine a scale of teeth of a user, where each imaging marker is located a predefined distance from the remaining imaging markers, and where the lip holder is to hold a cheek away from a mouth of a user to expose teeth of the user. A mobile device holder can include elements to receive a mobile device to capture images of the patient's teeth.

28 Claims, 13 Drawing Sheets

(51) Int. Cl.
| | |
|---|---|
| *A61C 9/00* | (2006.01) |
| *A61C 13/34* | (2006.01) |
| *G06T 7/70* | (2017.01) |
| *A61C 5/90* | (2017.01) |
| *H04B 1/3877* | (2015.01) |
| *G06T 7/60* | (2017.01) |
| *A61B 1/00* | (2006.01) |
| *G06T 7/62* | (2017.01) |
| *G06T 7/73* | (2017.01) |

(52) U.S. Cl.
CPC .............. *A61C 13/34* (2013.01); *A61C 19/04* (2013.01); *G06T 7/60* (2013.01); *G06T 7/62* (2017.01); *G06T 7/70* (2017.01); *G06T 7/74* (2017.01); *H04B 1/3877* (2013.01); *A61C 9/0053* (2013.01); *G06T 2207/10016* (2013.01); *G06T 2207/30036* (2013.01); *G06T 2207/30204* (2013.01)

(58) Field of Classification Search
CPC . G06T 2207/30036; G06T 2207/10016; G06T 2207/30204; H04B 1/3877
USPC ........................................................ 433/140
See application file for complete search history.

(56) References Cited

U.S. PATENT DOCUMENTS

| | | |
|---|---|---|
| 2,467,432 A | 4/1949 | Kesling |
| 2,531,222 A | 11/1950 | Kesling |
| 2,835,628 A | 5/1958 | Saffir |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,503,127 A | 3/1970 | Kasdin et al. |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,813,781 A | 6/1974 | Forgione |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,039,653 A | 8/1977 | DeFoney et al. |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,278,087 A | 7/1981 | Theeuwes |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,450,150 A | 5/1984 | Sidman |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,741,700 A | 5/1988 | Barabe |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,818,542 A | 4/1989 | De Luca et al. |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,861,268 A | 8/1989 | Garay et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,968,251 A | 11/1990 | Darnell |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,049,077 A | 9/1991 | Goldin et al. |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |

(56) References Cited

U.S. PATENT DOCUMENTS

| | | | |
|---|---|---|---|
| 5,103,838 | A | 4/1992 | Yousif |
| 5,114,339 | A | 5/1992 | Guis |
| 5,121,333 | A | 6/1992 | Riley et al. |
| 5,123,425 | A | 6/1992 | Shannon et al. |
| 5,128,870 | A | 7/1992 | Erdman et al. |
| 5,130,064 | A | 7/1992 | Smalley et al. |
| 5,131,843 | A | 7/1992 | Hilgers et al. |
| 5,131,844 | A | 7/1992 | Marinaccio et al. |
| 5,139,419 | A | 8/1992 | Andreiko et al. |
| 5,145,364 | A | 9/1992 | Martz et al. |
| 5,176,517 | A | 1/1993 | Truax |
| 5,194,003 | A | 3/1993 | Garay et al. |
| 5,204,670 | A | 4/1993 | Stinton |
| 5,222,499 | A | 6/1993 | Allen et al. |
| 5,224,049 | A | 6/1993 | Mushabac |
| 5,238,404 | A | 8/1993 | Andreiko |
| 5,242,304 | A | 9/1993 | Truax et al. |
| 5,245,592 | A | 9/1993 | Kuemmel et al. |
| 5,273,429 | A | 12/1993 | Rekow et al. |
| 5,278,756 | A | 1/1994 | Lemchen et al. |
| 5,306,144 | A | 4/1994 | Hibst et al. |
| 5,314,335 | A | 5/1994 | Fung |
| 5,324,186 | A | 6/1994 | Bakanowski |
| 5,328,362 | A | 7/1994 | Watson et al. |
| 5,335,657 | A | 8/1994 | Terry et al. |
| 5,338,198 | A | 8/1994 | Wu et al. |
| 5,340,309 | A | 8/1994 | Robertson |
| 5,342,202 | A | 8/1994 | Deshayes |
| 5,344,315 | A | 9/1994 | Hanson |
| 5,368,478 | A | 11/1994 | Andreiko et al. |
| 5,372,502 | A | 12/1994 | Massen et al. |
| D354,355 | S | 1/1995 | Hilgers |
| 5,382,164 | A | 1/1995 | Stern |
| 5,395,238 | A | 3/1995 | Andreiko et al. |
| 5,415,542 | A | 5/1995 | Kesling |
| 5,431,562 | A | 7/1995 | Andreiko et al. |
| 5,440,326 | A | 8/1995 | Quinn |
| 5,440,496 | A | 8/1995 | Andersson et al. |
| 5,447,432 | A | 9/1995 | Andreiko et al. |
| 5,449,703 | A | 9/1995 | Mitra et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,487,662 | A | 1/1996 | Kipke et al. |
| RE35,169 | E | 3/1996 | Lemchen et al. |
| 5,499,633 | A | 3/1996 | Fenton |
| 5,522,725 | A | 6/1996 | Jordan et al. |
| 5,528,735 | A | 6/1996 | Strasnick et al. |
| 5,533,895 | A | 7/1996 | Andreiko et al. |
| 5,540,732 | A | 7/1996 | Testerman |
| 5,542,842 | A | 8/1996 | Andreiko et al. |
| 5,543,780 | A | 8/1996 | McAuley et al. |
| 5,549,476 | A | 8/1996 | Stern |
| 5,562,448 | A | 10/1996 | Mushabac |
| 5,570,182 | A | 10/1996 | Nathel et al. |
| 5,575,655 | A | 11/1996 | Darnell |
| 5,583,977 | A | 12/1996 | Seidl |
| 5,587,912 | A | 12/1996 | Andersson et al. |
| 5,588,098 | A | 12/1996 | Chen et al. |
| 5,605,459 | A | 2/1997 | Kuroda et al. |
| 5,607,305 | A | 3/1997 | Andersson et al. |
| 5,614,075 | A | 3/1997 | Andre |
| 5,621,648 | A | 4/1997 | Crump |
| 5,626,537 | A | 5/1997 | Danyo et al. |
| 5,636,736 | A | 6/1997 | Jacobs et al. |
| 5,645,420 | A | 7/1997 | Bergersen |
| 5,645,421 | A | 7/1997 | Slootsky |
| 5,651,671 | A | 7/1997 | Seay et al. |
| 5,655,653 | A | 8/1997 | Chester |
| 5,659,420 | A | 8/1997 | Wakai et al. |
| 5,683,243 | A | 11/1997 | Andreiko et al. |
| 5,683,244 | A | 11/1997 | Truax |
| 5,691,539 | A | 11/1997 | Pfeiffer |
| 5,692,894 | A | 12/1997 | Schwartz et al. |
| 5,711,665 | A | 1/1998 | Adam et al. |
| 5,711,666 | A | 1/1998 | Hanson |
| 5,725,376 | A | 3/1998 | Poirier |
| 5,725,378 | A | 3/1998 | Wang |
| 5,730,151 | A | 3/1998 | Summer et al. |
| 5,737,084 | A | 4/1998 | Ishihara |
| 5,740,267 | A | 4/1998 | Echerer et al. |
| 5,742,700 | A | 4/1998 | Yoon et al. |
| 5,769,631 | A | 6/1998 | Williams |
| 5,774,425 | A | 6/1998 | Ivanov et al. |
| 5,790,242 | A | 8/1998 | Stern et al. |
| 5,799,100 | A | 8/1998 | Clarke et al. |
| 5,800,162 | A | 9/1998 | Shimodaira et al. |
| 5,800,174 | A | 9/1998 | Andersson |
| 5,813,854 | A | 9/1998 | Nikodem |
| 5,816,800 | A | 10/1998 | Brehm et al. |
| 5,818,587 | A | 10/1998 | Devaraj et al. |
| 5,823,778 | A | 10/1998 | Schmitt et al. |
| 5,848,115 | A | 12/1998 | Little et al. |
| 5,857,853 | A | 1/1999 | van Nifterick et al. |
| 5,866,058 | A | 2/1999 | Batchelder et al. |
| 5,876,199 | A | 3/1999 | Bergersen |
| 5,879,158 | A | 3/1999 | Doyle et al. |
| 5,880,961 | A | 3/1999 | Crump |
| 5,880,962 | A | 3/1999 | Andersson et al. |
| 5,882,192 | A * | 3/1999 | Bergersen ................ A61C 7/00 433/2 |
| 5,886,702 | A | 3/1999 | Migdal et al. |
| 5,890,896 | A | 4/1999 | Padial |
| 5,904,479 | A | 5/1999 | Staples |
| 5,911,576 | A | 6/1999 | Ulrich et al. |
| 5,934,288 | A | 8/1999 | Avila et al. |
| 5,957,686 | A | 9/1999 | Anthony |
| 5,964,587 | A | 10/1999 | Sato |
| 5,971,754 | A | 10/1999 | Sondhi et al. |
| 5,975,893 | A | 11/1999 | Chishti et al. |
| 5,975,906 | A | 11/1999 | Knutson |
| 5,980,246 | A | 11/1999 | Ramsay et al. |
| 5,989,023 | A | 11/1999 | Summer et al. |
| 5,993,413 | A | 11/1999 | Aaltonen et al. |
| 6,002,706 | A | 12/1999 | Stayer et al. |
| 6,018,713 | A | 1/2000 | Coli et al. |
| 6,044,309 | A | 3/2000 | Honda |
| 6,049,743 | A | 4/2000 | Baba |
| 6,053,731 | A | 4/2000 | Heckenberger |
| 6,068,482 | A | 5/2000 | Snow |
| 6,070,140 | A | 5/2000 | Tran |
| 6,099,303 | A | 8/2000 | Gibbs et al. |
| 6,099,314 | A | 8/2000 | Kopelman et al. |
| 6,102,701 | A | 8/2000 | Engeron |
| 6,120,287 | A | 9/2000 | Chen |
| 6,123,544 | A | 9/2000 | Cleary |
| 6,152,731 | A | 11/2000 | Jordan et al. |
| 6,154,676 | A | 11/2000 | Levine |
| 6,183,248 | B1 | 2/2001 | Chishti et al. |
| 6,183,249 | B1 | 2/2001 | Brennan et al. |
| 6,186,780 | B1 | 2/2001 | Hibst et al. |
| 6,190,165 | B1 | 2/2001 | Andreiko et al. |
| 6,200,133 | B1 | 3/2001 | Kittelsen |
| 6,201,880 | B1 | 3/2001 | Elbaum et al. |
| 6,210,162 | B1 | 4/2001 | Chishti et al. |
| 6,212,435 | B1 | 4/2001 | Lattner et al. |
| 6,213,767 | B1 | 4/2001 | Dixon et al. |
| 6,217,334 | B1 | 4/2001 | Hultgren |
| 6,227,850 | B1 | 5/2001 | Chishti et al. |
| 6,230,142 | B1 | 5/2001 | Benigno et al. |
| 6,231,338 | B1 | 5/2001 | de Josselin de Jong et al. |
| 6,239,705 | B1 | 5/2001 | Glen |
| 6,243,601 | B1 | 6/2001 | Ovist |
| 6,263,234 | B1 | 7/2001 | Engelhardt et al. |
| 6,283,761 | B1 | 9/2001 | Joao |
| 6,288,138 | B1 | 9/2001 | Yamamoto |
| 6,299,438 | B1 | 10/2001 | Sahagian et al. |
| 6,309,215 | B1 | 10/2001 | Phan et al. |
| 6,313,432 | B1 | 11/2001 | Nagata et al. |
| 6,315,553 | B1 | 11/2001 | Sachdeva et al. |
| 6,328,745 | B1 | 12/2001 | Ascherman |
| 6,332,774 | B1 | 12/2001 | Chikami |
| 6,334,073 | B1 | 12/2001 | Levine |

(56) References Cited

U.S. PATENT DOCUMENTS

| | | |
|---|---|---|
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B1 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 * | 1/2006 | Haywood ............... A61C 5/90 433/140 |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,156,663 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,194,781 B1 | 3/2007 | Orjela |
| 7,217,131 B2 | 5/2007 | Vuillemot |
| 7,220,122 B2 | 5/2007 | Chishti |
| 7,220,124 B2 | 5/2007 | Taub et al. |

(56) References Cited

U.S. PATENT DOCUMENTS

| | | |
|---|---|---|
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,108,189 B2 | 1/2012 | Chelnokov et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,152,518 B2 | 4/2012 | Kuo |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,753,114 B2 | 6/2014 | Vuillemot |
| 8,767,270 B2 | 7/2014 | Curry et al. |

(56) References Cited

U.S. PATENT DOCUMENTS

| | | |
|---|---|---|
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,948,482 B2 | 2/2015 | Levin |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,261,358 B2 | 2/2016 | Atiya et al. |
| 9,277,972 B2 | 3/2016 | Brandt et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,675,427 B2 | 6/2017 | Kopelman |
| 9,675,430 B2 | 6/2017 | Verker et al. |
| 9,693,839 B2 | 7/2017 | Atiya et al. |
| 9,730,769 B2 | 8/2017 | Chen et al. |
| 9,744,006 B2 | 8/2017 | Ross |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 9,861,451 B1 | 1/2018 | Davis |
| 9,936,186 B2 | 4/2018 | Jesenko et al. |
| 10,123,706 B2 | 11/2018 | Elbaz et al. |
| 10,123,853 B2 | 11/2018 | Moss et al. |
| 10,154,889 B2 | 12/2018 | Chen et al. |
| 10,159,541 B2 | 12/2018 | Bindayel |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,248,883 B2 | 4/2019 | Borovinskih et al. |
| 10,258,432 B2 | 4/2019 | Webber |
| 10,275,862 B2 | 4/2019 | Levin |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0008259 A1 | 1/2003 | Kuo et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0211440 A1 | 11/2003 | Kuo et al. |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Thou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1* | 5/2005 | Kerschbaumer ..... A61B 1/0676 396/16 |

(56) References Cited

U.S. PATENT DOCUMENTS

| | | |
|---|---|---|
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0196039 A1* | 9/2005 | Bengel ............... G06T 7/90 382/162 |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115782 A1 | 6/2006 | Li et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0207434 A1 | 9/2007 | Kuo et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0145812 A1* | 6/2008 | Taub ............... A61C 7/146 433/3 |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1* | 8/2010 | Weinlaender ......... A61B 1/247 600/476 |
| 2010/0231577 A1 | 9/2010 | Kim et al. |
| 2010/0268363 A1 | 10/2010 | Karim et al. |

(56) References Cited

U.S. PATENT DOCUMENTS

| | | |
|---|---|---|
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0065060 A1 | 3/2011 | Teixeira et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0212420 A1 | 9/2011 | Vuillemot |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0028210 A1 | 2/2012 | Hegyi et al. |
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0325431 A1 | 12/2013 | See et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0122027 A1 | 5/2014 | Andreiko et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0265034 A1 | 9/2014 | Dudley |
| 2014/0272774 A1 | 9/2014 | Dillon et al. |
| 2014/0280376 A1 | 9/2014 | Kuo |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1* | 11/2014 | Fleer .................. A61C 5/44 433/27 |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0004553 A1 | 1/2015 | Li et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0150501 A1 | 6/2015 | George et al. |
| 2015/0164335 A1 | 6/2015 | Van Der Poel et al. |
| 2015/0173856 A1 | 6/2015 | Iowe et al. |
| 2015/0182303 A1 | 7/2015 | Abraham et al. |
| 2015/0216626 A1 | 8/2015 | Ranjbar |
| 2015/0216716 A1 | 8/2015 | Anitua Aldecoa |
| 2015/0230885 A1 | 8/2015 | Wucher |
| 2015/0238073 A1* | 8/2015 | Charles .................. A61B 1/04 600/102 |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0351638 A1 | 12/2015 | Amato |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0022185 A1 | 1/2016 | Agarwal et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0100908 A1* | 4/2016 | Tesar .................. A61B 1/051 600/202 |
| 2016/0100924 A1 | 4/2016 | Wilson et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2016/0367188 A1 | 12/2016 | Malik et al. |
| 2016/0367339 A1 | 12/2016 | Khardekar et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049326 A1 | 2/2017 | Alfano et al. |
| 2017/0056131 A1 | 3/2017 | Alauddin et al. |
| 2017/0071705 A1 | 3/2017 | Kuo |

(56) References Cited

U.S. PATENT DOCUMENTS

| | | |
|---|---|---|
| 2017/0086943 A1 | 3/2017 | Mah |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0251954 A1 | 9/2017 | Lotan et al. |
| 2017/0258555 A1 | 9/2017 | Kopelman |
| 2017/0265970 A1 | 9/2017 | Verker |
| 2017/0281313 A1* | 10/2017 | Kim ............... A61C 7/08 |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2017/0340415 A1 | 11/2017 | Choi et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0055602 A1 | 3/2018 | Kopelman et al. |
| 2018/0071054 A1 | 3/2018 | Ha |
| 2018/0071055 A1 | 3/2018 | Kuo |
| 2018/0085059 A1 | 3/2018 | Lee |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2018/0280118 A1 | 10/2018 | Cramer |
| 2018/0284727 A1 | 10/2018 | Cramer et al. |
| 2018/0318043 A1 | 11/2018 | Li et al. |
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0026599 A1 | 1/2019 | Salah et al. |
| 2019/0029522 A1 | 1/2019 | Sato et al. |
| 2019/0029784 A1 | 1/2019 | Moalem et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076026 A1 | 3/2019 | Elbaz et al. |
| 2019/0076214 A1 | 3/2019 | Nyukhtikov et al. |
| 2019/0076216 A1 | 3/2019 | Moss et al. |
| 2019/0090983 A1 | 3/2019 | Webber et al. |
| 2019/0095539 A1 | 3/2019 | Elbaz et al. |
| 2019/0099129 A1 | 4/2019 | Kopelman et al. |
| 2019/0105130 A1 | 4/2019 | Grove et al. |
| 2019/0125494 A1 | 5/2019 | Li et al. |
| 2019/0152152 A1 | 5/2019 | O'Leary et al. |
| 2019/0160590 A1 | 5/2019 | Culp |
| 2019/0171618 A1 | 6/2019 | Kuo |
| 2019/0175303 A1 | 6/2019 | Akopov et al. |
| 2019/0175304 A1 | 6/2019 | Morton et al. |
| 2019/0183614 A1 | 6/2019 | Levin |

FOREIGN PATENT DOCUMENTS

| | | |
|---|---|---|
| CA | 1121955 A1 | 4/1982 |
| CN | 1655732 A | 8/2005 |
| CN | 1655733 A | 8/2005 |
| CN | 1867317 A | 11/2006 |
| CN | 102017658 A | 4/2011 |
| CN | 103889364 A | 6/2014 |
| CN | 204092220 U | 1/2015 |
| CN | 105496575 A | 4/2016 |
| CN | 105997274 A | 10/2016 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 04-028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20070108019 A | 11/2007 |
| KR | 10-20090065778 A | 6/2009 |
| KR | 10-1266966 B1 | 5/2013 |
| KR | 10-2016-041632 A | 4/2016 |
| KR | 10-2016-0071127 A | 6/2016 |
| KR | 10-1675089 B1 | 11/2016 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO02/017776 A2 | 3/2002 |
| WO | WO02/024100 A1 | 3/2002 |
| WO | WO02/058583 A1 | 8/2002 |
| WO | WO02/062252 A1 | 8/2002 |
| WO | WO02/095475 A1 | 11/2002 |
| WO | WO03/003932 A2 | 1/2003 |
| WO | WO2005/114183 A1 | 12/2005 |
| WO | WO2006/096558 A2 | 9/2006 |
| WO | WO2006/100700 A1 | 9/2006 |

(56) References Cited

FOREIGN PATENT DOCUMENTS

| | | |
|---|---|---|
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | 2009040010 A1 | 4/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | 2014143911 A1 | 9/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | 2016116854 A1 | 7/2016 |
| WO | WO2016/113745 A1 | 7/2016 |
| WO | WO2016/200177 A1 | 12/2016 |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |
| WO | WO2018/232113 A1 | 12/2018 |
| WO | WO2019/018784 A1 | 1/2019 |

OTHER PUBLICATIONS

US 10,342,434 B2, 07/2019, Elbaz et al. (withdrawn)
AADR. American Association for Dental Research; Summary of Activities; Los Angeles, CA; p. 195; Mar. 20-23,(year of pub. sufficiently earlier than effective US filing date and any foreign priority date) 1980.
Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.
Alexander et al.; The DigiGraph Work Station Part 2 Clinical Management; J. Clin. Orthod.; pp. 402-407; (Author Manuscript); Jul. 1990.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Allesee Orthodontic Appliance: Important Tip About Wearing the Red White & Blue Active Clear Retainer System; Allesee Orthodontic Appliances-Pro Lab; 1 page; (year of pub. sufficiently earlier than effective US filing date and any foreign priority date); 1998.
Allesee Orthodontic Appliances: DuraClearTM; Product information; 1 page; (year of pub. sufficiently earlier than effective US filing date and any foreign priority date) 1997.
Allesee Orthodontic Appliances; The Choice Is Clear: Red, White & Blue . . . The Simple, Affordable, No-Braces Treatment; (product information for doctors); retrieved from the internet (http://ormco.com/aoa/appliancesservices/RWB/doctorhtml); 5 pages on May 19, 2003.
Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Arakawa et al; Mouthguard biosensor with telemetry system for monitoring of saliva glucose: A novel cavitas sensor; Biosensors and Bioelectronics; 84; pp. 106-111; Oct. 2016.
Bandodkar et al.; All-printed magnetically self-healing electrochemical devices; Science Advances; 2(11); 11 pages; e1601465; Nov. 2016.
Bandodkar et al.; Self-healing inks for autonomous repair of printable electrochemical devices; Advanced Electronic Materials; 1(12); 5 pages; 1500289; Dec. 2015.
Bandodkar et al.; Wearable biofuel cells: a review; Electroanalysis; 28(6); pp. 1188-1200; Jun. 2016.
Bandodkar et al.; Wearable chemical sensors: present challenges and future prospects; Acs Sensors; 1(5); pp. 464-482; May 11, 2016.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

(56) References Cited

OTHER PUBLICATIONS

Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Begole et al.; A Computer System for the Analysis of Dental Casts; The Angle Orthodontist; 51(3); pp. 252-258; Jul. 1981.
Berland; The use of smile libraries for cosmetic dentistry; Dental Tribune: Asia Pacific Edition; pp. 16-18; Mar. 29, 2006.
Bernabe et al.; Are the lower incisors the best predictors for the unerupted canine and premolars sums? An analysis of peruvian sample; The Angle Orthodontist; 75(2); pp. 202-207; Mar. 2005.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(I); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bookstein; Principal warps: Thin-plate splines and decomposition of deformations; IEEE Transactions on pattern analysis and machine intelligence; 11(6); pp. 567-585; Jun. 1989.
Bourke, Coordinate System Transformation; 1 page; retrived from the internet (http://astronomy.swin.edu.au/'pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on The Uses of the Computer in Orthodontic Practice (Part 1); Journal of Clinical Orthodontics; 13(7); pp. 442-453; (interview); Jul. 1979.
Burstone; Dr. Charles J. Burstone on The Uses of the Computer in Orthodontic Practice (Part 2); journal of Clinical Orthodontics; 13(8); pp. 539-551 (interview); Aug. 1979.
Cadent Inc.; OrthoCAD ABO user guide; 38 pages; Dec. 21, 2005.
Cadent Inc.; Reviewing and modifying an orthoCAD case; 4 pages; Feb. 14, 2005.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Collins English Dictionary; Teeth (definition); 9 pages; retrieved from the internet (https:www.collinsdictionary.com/us/dictionary/english/teeth) on May 13, 2019.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret ' A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
CSI Computerized Scanning and Imaging Facility; What is a maximum/minimum intensity projection (Mip/MinIP); 1 page; retrived from the internet (http://csi.whoi.edu/content/what-maximumminimum-intensity-projection-mipminip); Jan. 4, 2010.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
Daniels et al.; The development of the index of complexity outcome and need (ICON); British Journal of Orthodontics; 27(2); pp. 149-162; Jun. 2000.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dentrix; Dentrix G3, new features; 2 pages; retrieved from the internet (http://www.dentrix.com/g3/new_features/index.asp); on Jun. 6, 2008.
Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Giacomo et al.; Clinical application of sterolithographic surgical guides for implant placement: Preliminary results; Journal Periodontolgy; 76(4); pp. 503-507; Apr. 2005.
Di Muzio et al.; Minimum intensity projection (MinIP); 6 pages; retrieved from the internet (https://radiopaedia.org/articles/minimum-intensity-projection-minip) on Sep. 6, 2018.
Dicom to surgical guides; (Screenshot)1 page; retrieved from the internet at YouTube (https://youtu.be/47KtOmCEFQk); Published Apr. 4, 2016.

(56) References Cited

OTHER PUBLICATIONS dictionary.com; Plural (definition); 6 pages; retrieved from the internet ( https://www.dictionary.com/browse/plural#) on May 13, 2019.
dictionary.com; Quadrant (definition); 6 pages; retrieved from the internet ( https://www.dictionary.com/browse/guadrant?s=t) on May 13, 2019.
Doruk et al.; The role of the headgear timer in extraoral co-operation; European Journal of Orthodontics; 26; pp. 289-291; Jun. 1, 2004.
Doyle; Digital Dentistry; Computer Graphics World; pp. 50-52 andp. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Ellias et al.; Proteomic analysis of saliva identifies potential biomarkers for orthodontic tooth movement; The Scientific World Journal; vol. 2012; Article ID 647240; dio:10.1100/2012/647240; 7 pages; Jul. 2012.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Farooq et al.; Relationship between tooth dimensions and malocclusion; JPMA: The Journal of the Pakistan Medical Association; 64(6); pp. 670-674; Jun. 2014.
Felton et al.; A Computerized Analysis of the Shape and Stability of Mandibular Arch Form; American Journal of Orthodontics and Dentofacial Orthopedics; 92(6); pp. 478-483; Dec. 1987.
Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.
Friede et al.; Accuracy of Cephalometric Prediction in Orthognathic Surgery; Journal of Oral and Maxillofacial Surgery; 45(9); pp. 754-760; Sep. 1987.
Friedrich et al; Measuring system for in vivo recording of force systems in orthodontic treatment-concept and analysis of accuracy; J. Biomech.; 32(1); pp. 81-85; (Abstract Only) Jan. 1999.
Futterling et al.; Automated Finite Element Modeling of a Human Mandible with Dental Implants; JS WSCG '98 —Conference Program; 8 pages; retrieved from the Internet (https://dspace5.zcu.cz/bitstream/11025/15851/1/Strasser_98.pdf); on Aug. 21, 2018.
Gansky; Dental data mining: potential pitfalls and practical issues; Advances in Dental Research; 17(1); pp. 109-114; Dec. 2003.
Gao et al.; 3-D element Generation for Multi-Connected Complex Dental and Mandibular Structure; IEEE Proceedings International Workshop in Medical Imaging and Augmented Reality; pp. 267-271; Jun. 12, 2001.
Geomagic; Dental reconstruction; 1 page; retrieved from the internet (http://geomagic.com/en/solutions/industry/detal_desc.php) on Jun. 6, 2008.
Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=068ArticleNum+); 21 pages; Jun. 1982.
Gottschalk et al.; OBBTree: A hierarchical structure for rapid interference detection; 12 pages; (http://www.cs.unc.edu/?geom/OBB/OBBT.html); retrieved from te internet (https://www.cse.iitk.ac.in/users/amit/courses/RMP/presentations/dslamba/presentation/sig96.pdf) on Apr. 25, 2019.
gpsdentaire.com; Get a realistic smile simulation in 4 steps with GPS; a smile management software; 10 pages; retrieved from the internet (http://www.gpsdentaire.com/en/preview/) on Jun. 6, 2008.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Grest, Daniel; Marker-Free Human Motion Capture in Dynamic Cluttered Environments from a Single View-Point, PhD Thesis; 171 pages; Dec. 2007.
Guess et al.; Computer Treatment Estimates in Orthodontics and Orthognathic Surgery; Journal of Clinical Orthodontics; 23(4); pp. 262- 268; 11 pages; (Author Manuscript); Apr. 1989.
Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . . ); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filing date and any foreign priority date) 1999.
Imani et al.; A wearable chemical-electrophysiological hybrid biosensing system for real-time health and fitness monitoring; Nature Communications; 7; 11650. doi 1038/ncomms11650; 7 pages; May 23, 2016.
Invisalign; You were made to move. There's never been a better time to straighten your teeth with the most advanced clear aligner in the world; Product webpage; 2 pages; retrieved from the internet (www.invisalign.com/) on Dec. 28, 2017.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jeerapan et al.; Stretchable biofuel cells as wearable textile-based self-powered sensors; Journal of Materials Chemistry A; 4(47); pp. 18342-18353; Dec. 21, 2016.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jia et al.; Epidermal biofuel cells: energy harvesting from human perspiration; Angewandle Chemie International Edition; 52(28); pp. 7233-7236; Jul. 8, 2013.

(56) References Cited

OTHER PUBLICATIONS

Jia et al.; Wearable textile biofuel cells for powering electronics; Journal of Materials Chemistry A; 2(43); pp. 18184-18189; Oct. 14, 2014.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Karaman et al.; A practical method of fabricating a lingual retainer; Am. Journal of Orthodontic and Dentofacial Orthopedics; 124(3); pp. 327-330; Sep. 2003.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kim et al.; A wearable fingernail chemical sensing platform: pH sensing at your fingertips; Talanta; 150; pp. 622-628; Apr. 2016.

Kim et al.; Advanced materials for printed wearable electrochemical devices: A review; Advanced Electronic Materials; 3(1); 15 pages; 1600260; Jan. 2017.

Kim et al.; Noninvasive alcohol monitoring using a wearable tatto-based iontophoretic-biosensing system; Acs Sensors; 1(8); pp. 1011-1019; Jul. 22, 2016.

Kim et al.; Non-invasive mouthguard biosensor for continuous salivary monitoring of metabolites; Analyst; 139(7); pp. 1632-1636; Apr. 7, 2014.

Kim et al.; Wearable salivary uric acid mouthguard biosensor with integrated wireless electronics; Biosensors and Bioelectronics; 74; pp. 1061-1068; 19 pages; (Author Manuscript); Dec. 2015.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.

Kumar et al.; Biomarkers in orthodontic tooth movement; Journal of Pharmacy Bioallied Sciences; 7(Suppl 2); pp. S325-S330; 12 pages; (Author Manuscript); Aug. 2015.

Kumar et al.; Rapid maxillary expansion: a unique treatment modality in dentistry; J. Clin. Diagn. Res.; 5(4); pp. 906-911; Aug. 2011.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Lawrence; Salivary markers of systemic disease: noninvasive diagnosis of disease and monitoring of general health; Journal of the Canadian Dental Association Clinical Practice; 68(3); pp. 170-174; Mar. 2002.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

Mantzikos et al.; Case report: Forced eruption and implant site development; The Angle Orthodontist; 68(2); pp. 179-186; Apr. 1998.

Martinelli et al.; Prediction of lower permanent canine and premolars width by correlation methods; The Angle Orthodontist; 75(5); pp. 805-808; Sep. 2005.

McCann; Inside the ADA; J. Amer. Dent. Assoc, 118:286-294; Mar. 1989.

McNamara et al.; Invisible Retainers; J. Clin Orthod.; pp. 570-578; 11 pages; (Author Manuscript); Aug. 1985.

McNamara et al.; Orthodontic and Orthopedic Treatment in the Mixed Dentition; Needham Press; pp. 347-353; Jan. 1993.

Methot; Get the picture with a gps for smile design in 3 steps; Spectrum; 5(4); pp. 100-105; (year of pub. sufficiently earlier than effective US filing date and any foreign priority date) 2006.

Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filed and any foreign priority date) 1987.

Moles; Correcting Mild Malalignments—As Easy As One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; CEREC CAD/CAM Inlays: Aesthetics and Durability in a Single Appointment; Dentistry Today; 9(8); pp. 20, 22-23 and 54; Oct. 1990.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.

Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.

Nishanian et al.; Oral fluids as an alternative to serum for measurement of markers of immune activation; Clinical and Diagnostic Laboratory Immunology; 5(4); pp. 507-512; Jul. 1998.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Nourallah et al.; New regression equations for prediciting the size of unerupted canines and premolars in a contemporary population; The Angle Orthodontist; 72(3); pp. 216-221; Jun. 2002.

Ogawa et al.; Mapping, profiling and clustering of pressure pain threshold (PPT) in edentulous oral muscosa; Journal of Dentistry; 32(3); pp. 219-228; Mar. 2004.

Ogimoto et al.; Pressure-pain threshold determination in the oral mucosa; Journal of Oral Rehabilitation; 29(7); pp. 620-626; Jul. 2002.

ormco.com; Increasing clinical performance with 3D interactive treatment planning and patient-specific appliances; 8 pages; retrieved from the internet (http://www.konsident.corn/wp-content/files_mf/1295385693http_ormco.com_index_cmsfilesystemaction_fileOrmcoPDF_whitepapers.pdf) on Feb. 27, 2019.

OrthoCAD downloads; retrieved Jun. 27, 2012 from the internet (www.orthocad.com/download/downloads.asp); 2 pp.; Feb. 14, 2005.

(56) References Cited

OTHER PUBLICATIONS

Page et al.; Validity and accuracy of a risk calculator in predicting periodontal disease; Journal of the American Dental Association; 133(5); pp. 569-576; May 2002.

Paredes et al.; A new, accurate and fast digital method to predict unerupted tooth size; The Angle Orthodontist; 76(1); pp. 14-19; Jan. 2006.

Parrilla et al.; A textile-based stretchable multi-ion potentiometric sensor; Advanced Healthcare Materials; 5(9); pp. 996-1001; May 2016.

Patterson Dental; Cosmetic imaging; 2 pages retrieved from the internet (http://patterson.eaglesoft.net/cnt_di_cosimg.html) on Jun. 6, 2008.

Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.

Pinkham; Foolish Concept Propels Technology; Dentist, 3 pages , Jan./Feb. 1989.

Pinkham; Inventor's CAD/CAM May Transform Dentistry; Dentist; pp. 1 and 35, Sep. 1990.

Ponitz; Invisible retainers; Am. J. Orthod.; 59(3); pp. 266-272; Mar. 1971.

Procera Research Projects; Procera Research Projects 1993 Abstract Collection; 23 pages; (year of pub. sufficiently earlier than effective US filing date and any foreign priority date) 1993.

Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.

Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.

Raintree Essix & Ars Materials, Inc., Raintree Essix, Technical Magazine Table of contents and Essix Appliances, 7 pages; retrieved from the internet (http://www.essix.com/magazine/defaulthtml) on Aug. 13, 1997.

Redmond et al.; Clinical Implications of Digital Orthodontics; American Journal of Orthodontics and Dentofacial Orthopedics; 117(2); pp. 240-242; Feb. 2000.

Rekow et al.; CAD/CAM for Dental Restorations—Some of the Curious Challenges; IEEE Transactions on Biomedical Engineering; 38(4); pp. 314-318; Apr. 1991.

Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.

Rekow; A Review of the Developments in Dental CAD/CAM Systems; Current Opinion in Dentistry; 2; pp. 25-33; Jun. 1992.

Rekow; CAD/CAM in Dentistry: A Historical Perspective and View of the Future; Journal Canadian Dental Association; 58(4); pp. 283, 287-288; Apr. 1992.

Rekow; Computer-Aided Design and Manufacturing in Dentistry: A Review of the State of the Art; Journal of Prosthetic Dentistry; 58(4); pp. 512-516; Dec. 1987.

Rekow; Dental CAD-CAM Systems: What is the State of the Art?; The Journal of the American Dental Association; 122(12); pp. 43-48; Dec. 1991.

Rekow; Feasibility of an Automated System for Production of Dental Restorations, Ph.D. Thesis; Univ. Of Minnesota, 250 pp., Nov. 1988.

Richmond et al.; the Development of the Par Index (Peer Assessment Rating): Reliability and Validity.; the European Journal of Orthodontics; 14(2); pp. 125-139; Apr. 1992.

Richmond et al.; the Development of a 3D Cast Analysis System; British Journal of Orthodontics; 13(1); pp. 53-54; Jan. 1986.

Richmond; Recording the Dental Cast in Three Dimensions; American Journal of Orthodontics and Dentofacial Orthopedics; 92(3); pp. 199-206; Sep. 1987.

Rose et al.; the role of orthodontics in implant dentistry; British Dental Journal; 201(12); pp. 753-764; Dec. 23, 2006.

Rubin et al.; Stress analysis of the human tooth using a three-dimensional finite element model; Journal of Dental Research; 62(2); pp. 82-86; Feb. 1983.

Rudge; Dental Arch Analysis: Arch Form, a Review of the Literature; the European Journal of Orthodontics; 3(4); pp. 279-284; Jan. 1981.

Sahm et al.; "Micro-Electronic Monitoring of Functional Appliance Wear"; Eur J Orthod.; 12(3); pp. 297-301; Aug., 1990.

Sahm; Presentation of a wear timer for the clarification of scientific questions in orthodontic orthopedics; Fortschritte der Kieferorthopadie; 51 (4); pp. 243-247; (Translation Included) Jul. 1990.

Sakuda et al.; Integrated Information-Processing System in Clinical Orthodontics: an Approach with Use of a Computer Network System; American Journal of Orthodontics and Dentofacial Orthopedics; 101(3); pp. 210-220; 20 pp.; (Author Manuscript) Mar. 1992.

Sarment et al.; Accuracy of implant placement with a sterolithographic surgical guide; journal of Oral and Maxillofacial Implants; 118(4); pp. 571-577; Jul. 2003.

Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.

Schellhas et al.; Three-Dimensional Computed Tomography in Maxillofacial Surgical Planning; Archives of Otolaryngology—Head and Neck Surgery; 114(4); pp. 438-442; Apr. 1988.

Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.

Shilliday; Minimizing finishing problems with the mini-positioner; American Journal of Orthodontics; 59(6); pp. 596-599; Jun. 1971.

Shimada et al.; Application of optical coherence tomography (OCT) for diagnosis of caries, cracks, and defects of restorations; Current Oral Health Reports; 2(2); pp. 73-80; Jun. 2015.

Siemens; CEREC—Computer-Reconstruction, High Tech in der Zahnmedizin; 15 pagesl; (Includes Machine Translation); (year of pub. sufficiently earlier than effective US filing date and any foreign priority date); 2004.

Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.

Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.

Smalley; Implants for tooth movement: Determining implant location and orientation: Journal of Esthetic and Restorative Dentistry; 7(2); pp. 62-72; Mar. 1995.

Smart Technology; Smile library II; 1 page; retrieved from the internet (http://smart-technology.net/) on Jun. 6, 2008.

Smile-Vision_The smile-vision cosmetic imaging system; 2 pages; retrieved from the internet (http://www.smile-vision.net/cos_imaging.php) on Jun. 6, 2008.

Sobral De Agular et al.; The gingival crevicular fluid as a source of biomarkers to enhance efficiency of orthodontic and functional treatment of growing patients; Bio. Med. Research International; vol. 2017; 7 pages; Article ID 3257235; (year of pub. sufficiently earlier than effective US filing date and any foreign priority date) 2017.

Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.

Sturman; Interactive Keyframe Animation of 3-D Articulated Models; Proceedings Graphics Interface '84; vol. 86; pp. 35-40; May-Jun. 1984.

(56) References Cited

OTHER PUBLICATIONS

Svec et al.; Molded rigid monolithic porous polymers: an inexpensive, efficient, and versatile alternative to beads for design of materials for numerous applications; Industrial and Engineering Chemistry Research; 38(1); pp. 34-48; Jan. 4, 1999.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thera Mon; "Microsensor"; 2 pages; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
U.S. Food and Drug Administration; Color additives; 3 pages; retrieved from the internet (https://websrchive.org/web/20070502213911/http://www.cfsan.fda.gov/~dms/col-toc.html); last known as May 2, 2007.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Vevin et al.; Pose estimation of teeth through crown-shape matching; In Medical Imaging: Image Processing of International Society of Optics and Photonics; vol. 4684; pp. 955-965; May 9, 2002.
Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Watson et al.; Pressures recorded at to denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Wiedmann; According to the laws of harmony to find the right tooth shape with assistance of the computer; Digital Dental News; 2nd vol.; pp. 0005-0008; (English Version Included); Apr. 2008.
Wikipedia; Palatal expansion; 3 pages; retrieved from the internet (https://en.wikipedia.org/wiki/Palatal_expansion) on Mar. 5, 2018.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Windmiller et al.; Wearable electrochemical sensors and biosensors: a review; Electroanalysis; 25(1); pp. 29-46; Jan. 2013.
Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Wolf; Three-dimensional structure determination of semi-transparent objects from holographic data; Optics Communications; 1(4); pp. 153-156; Sep. 1969.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Kong Dental Journal; 3(2); pp. 107-115; Dec. 2006.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yaltara Software; Visual planner; 1 page; retrieved from the internet (http://yaltara.com/vp/) on Jun. 6, 2008.
Yamada et al.; Simulation of fan-beam type optical computed-tomography imaging of strongly scattering and weakly absorbing media; Applied Optics; 32(25); pp. 4808-4814; Sep. 1, 1993.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.

(56) References Cited

OTHER PUBLICATIONS

Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Zhang et al.; Visual speech features extraction for improved speech recognition; 2002 IEEE International conference on Acoustics, Speech and Signal Processing; vol. 2; 4 pages; May 13-17, 2002.
Zhou et al.; Biofuel cells for self-powered electrochemical biosensing and logic biosensing: A review; Electroanalysis; 24(2); pp. 197-209; Feb. 2012.
Zhou et al.; Bio-logic analysis of injury biomarker patterns in human serum samples; Talanta; 83(3); pp. 955-959; Jan. 15, 2011.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." filed Dec. 24, 2018.
Kopleman et al., U.S. Appl. No. 16/220,381 entitled "Closed loop adaptive orthodontic treatment methods and apparatuses," filed Dec. 14, 2018.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Culp; U.S. Appl. No. 16/236,220 entitled "Laser cutting," filed Dec. 28, 2018.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Chen et al.; U.S. Appl. No. 16/223,019 entitled "Release agent receptacle," filed Dec. 17, 2018.
"EClinger Selfie", https://play.google.com/store/apps/details?id=parkelict.ecligner, accessed Feb. 13, 2018, 1 page.
Dental Monitoring, "Basics : How to put your Cheek Retractor? (Dental Monitoring Tutorial)", https://www.youtube.com/watch?v=6K1HXw4Kq3c, May 27, 2016.
Dental Monitoring, "Dental Monitoring tutorial", https://www.youtube.com/watch?v=Dbe3udOf9_c, Mar. 18, 2015.

* cited by examiner

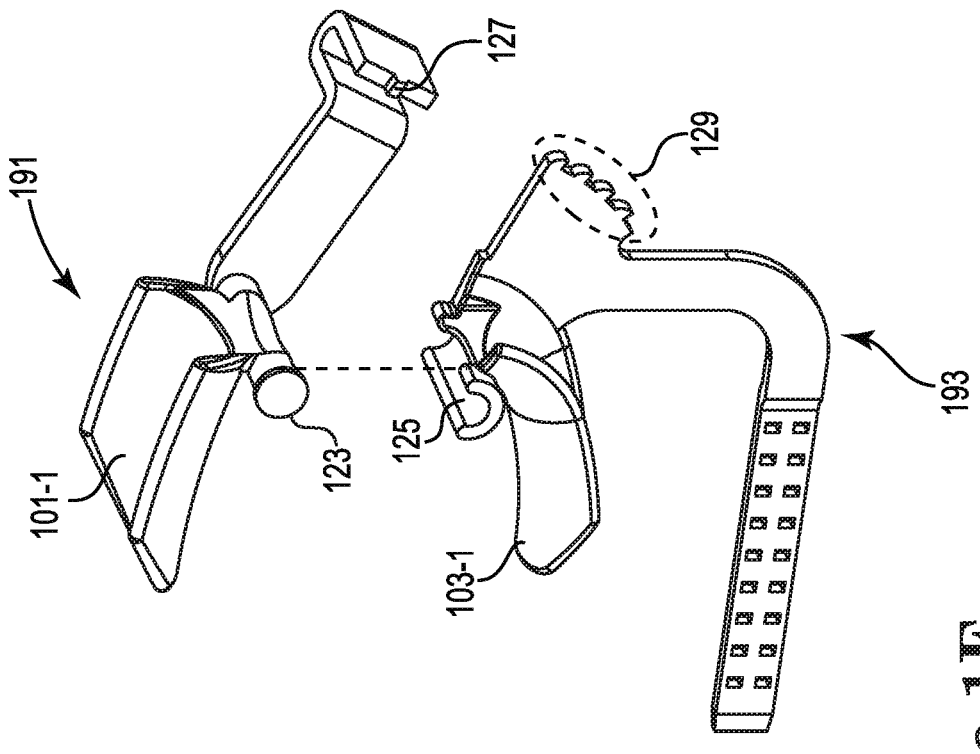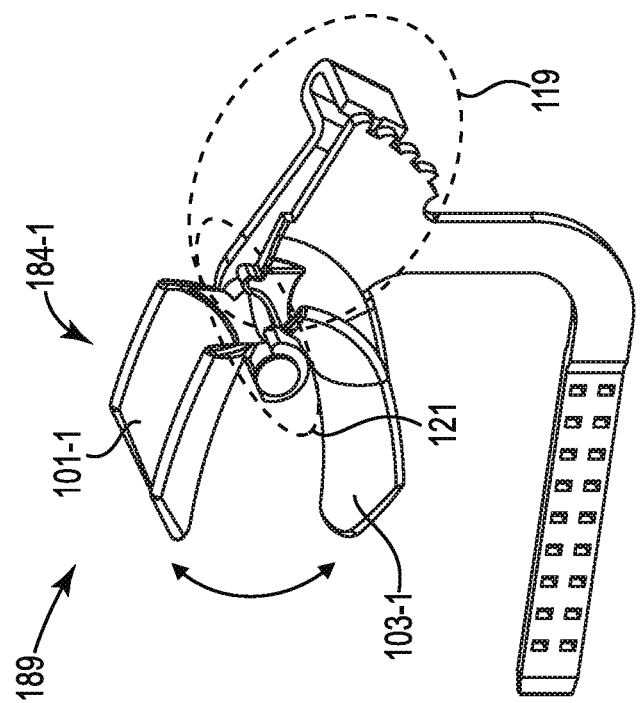
Figure 1E

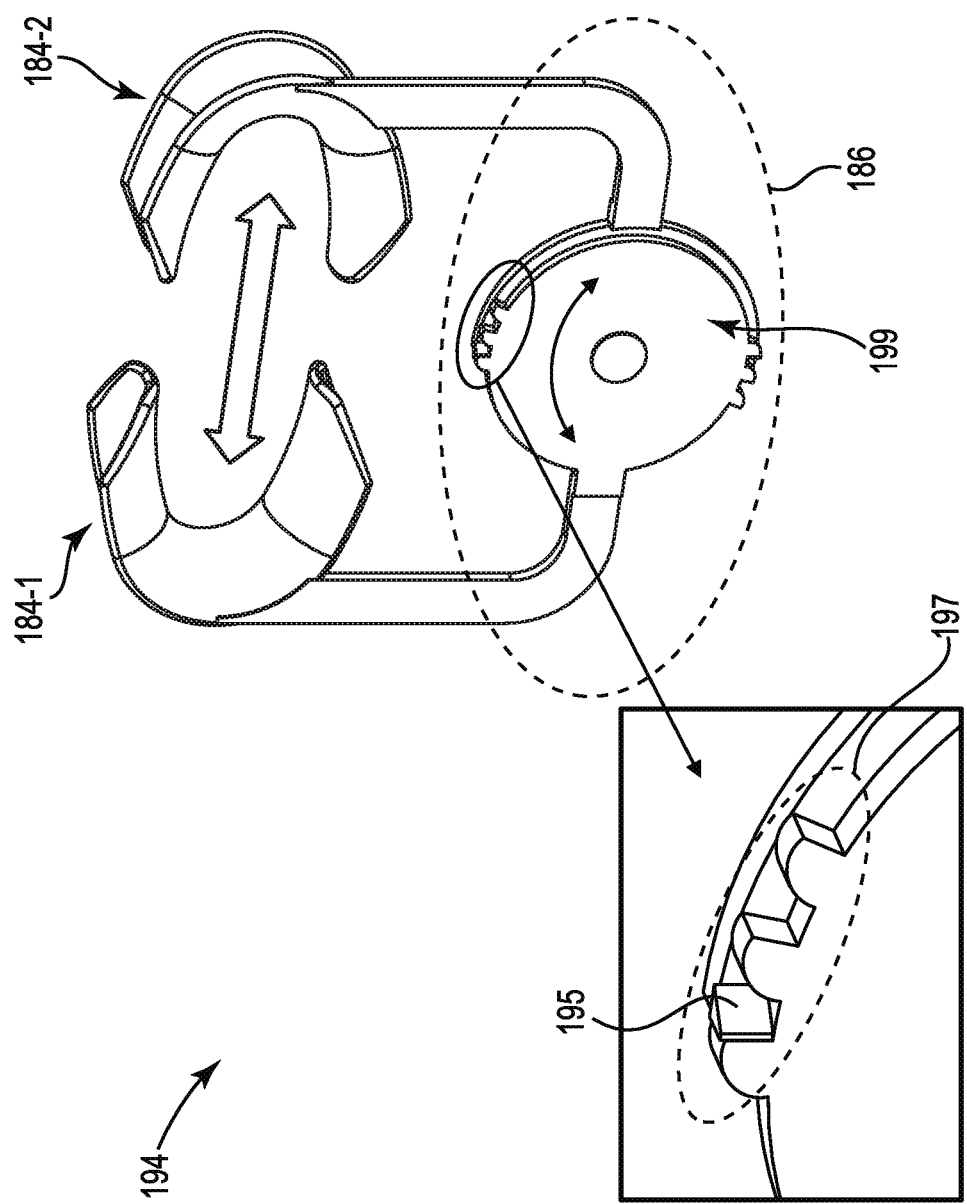

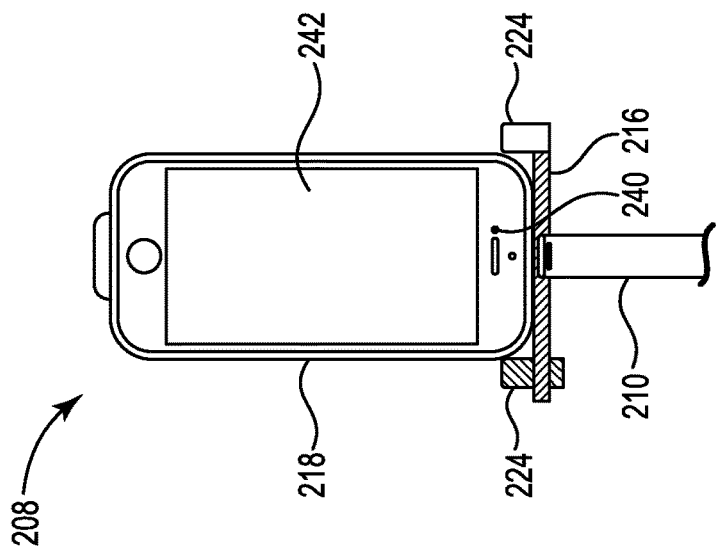
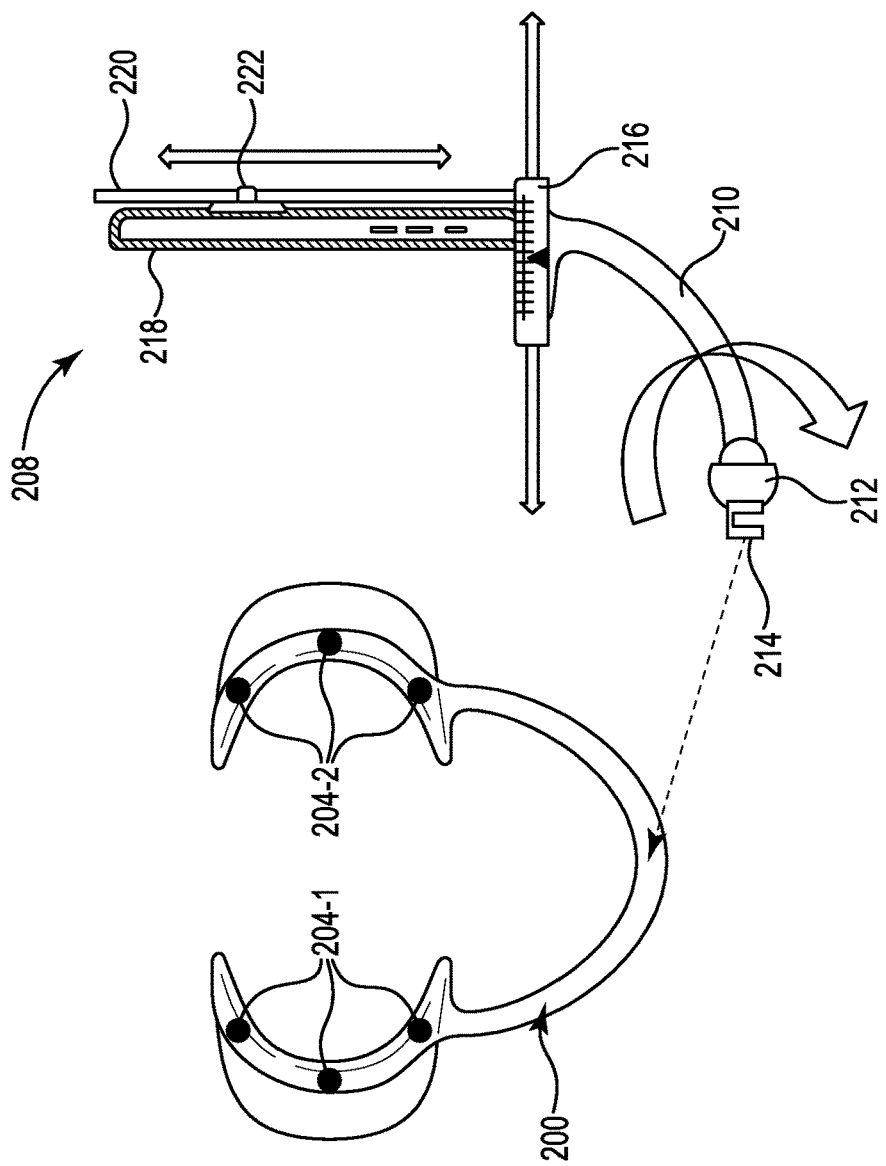
Figure 2B
Figure 2A

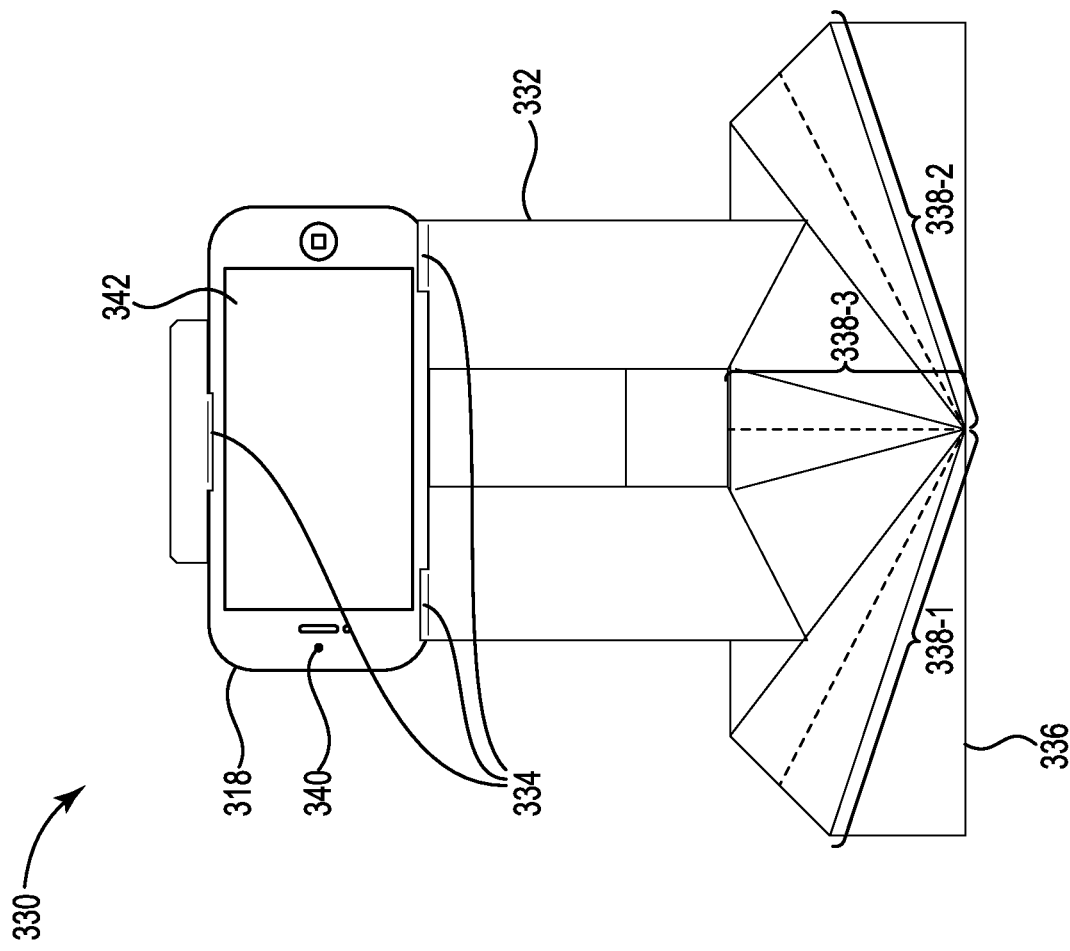

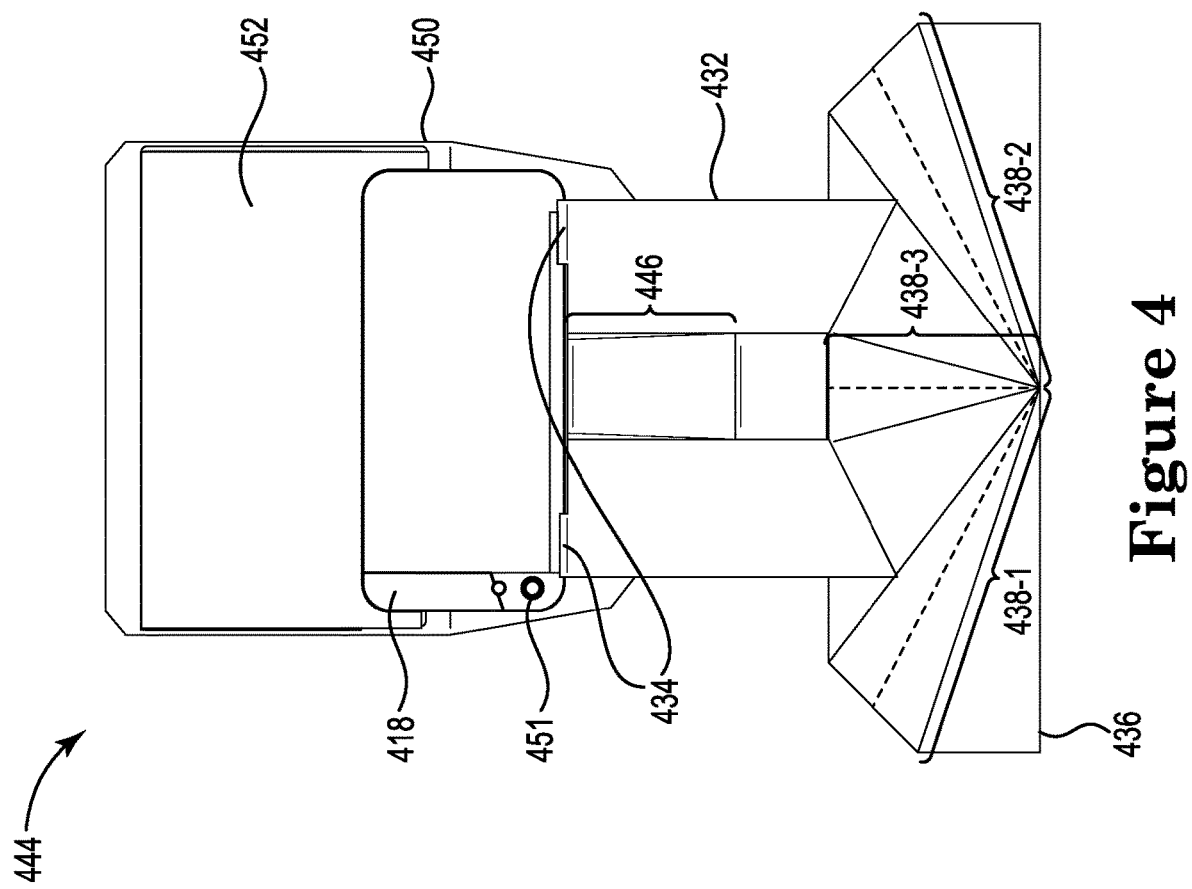

CHEEK RETRACTOR AND MOBILE DEVICE HOLDER

BACKGROUND

The present disclosure provides devices, computing device readable medium, and systems that utilize a cheek retractor and/or a mobile device holder for case assessment and/or dental treatments. Dental treatments involve restorative and/or orthodontic procedures to improve the quality of life of a patient.

For example, restorative procedures may be designed to implant a dental prosthesis (e.g., a crown, bridge, inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth or a jaw of a patient over a period of time.

As an example, orthodontic repositioning may be provided through a dental process that uses positioning appliances for realigning teeth. Such appliances may utilize a shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement. Appliances can also be used for other dental conditions, such as application of medications, appliances to help with sleep apnea, and other issues.

Such systems typically utilize a set of appliances that can be used serially such that, as the teeth move, a new appliance from the set can be implemented to further move the teeth without having to take a new impression of the patient's teeth at every increment of tooth movement in order to make each successive appliance. The same attachments may be utilized or attachments may be added, removed, or replaced with other attachment shapes that may impart different force characteristics than a previous appliance and attachment combination (i.e., appliance and one or more attachments).

Dental treatments with a set of appliances may involve repeated patient visits to an orthodontist in order to verify the dental treatment is proceeding as anticipated. For instance, an orthodontist may determine during a patient visit that the orthodontic procedure, such as repositioning misaligned teeth, is not proceeding as planned and may alter the procedure. Further, a prospective patient may visit an orthodontist to determine whether a dental treatment can work for the particular patient.

Visits to a treatment professional, such as an orthodontist, can be time consuming. A patient and/or a prospective patient may need to significantly alter their daily schedule in order to visit an orthodontist. Therefore, using a camera to take images of patients and/or prospective patients teeth may be utilized to track progress of a patient's dental treatment and/or determine whether the dental treatment will work on a prospective patient. Sending photos to an orthodontist or other practitioner can obfuscate the need for repeated visits to an orthodontist.

However, the process of taking photographs of a patients teeth can be cumbersome without assistance. For instance, a patient may require an additional person to assist them in taking clear photographs of that patient's teeth at different times during the dental treatment. Further, the distances and angles from the teeth of the patient may vary by image, resulting in inconsistencies between consecutive images and/or inconsistencies in images between different periods of the dental treatment process.

BRIEF DESCRIPTION OF THE DRAWINGS

FIG. 2A illustrates a front view of a cheek retractor and a side view of a mobile device holder according to a number of embodiments of the present disclosure.

FIG. 2B illustrates a front view of a mobile device holder according to a number of embodiments of the present disclosure.

FIG. 3 illustrates a front view of a mobile device holder according to a number of embodiments of the present disclosure.

FIG. 4 illustrates a front view of a mobile device holder according to a number of embodiments of the present disclosure.

DETAILED DESCRIPTION

Figure 1A:
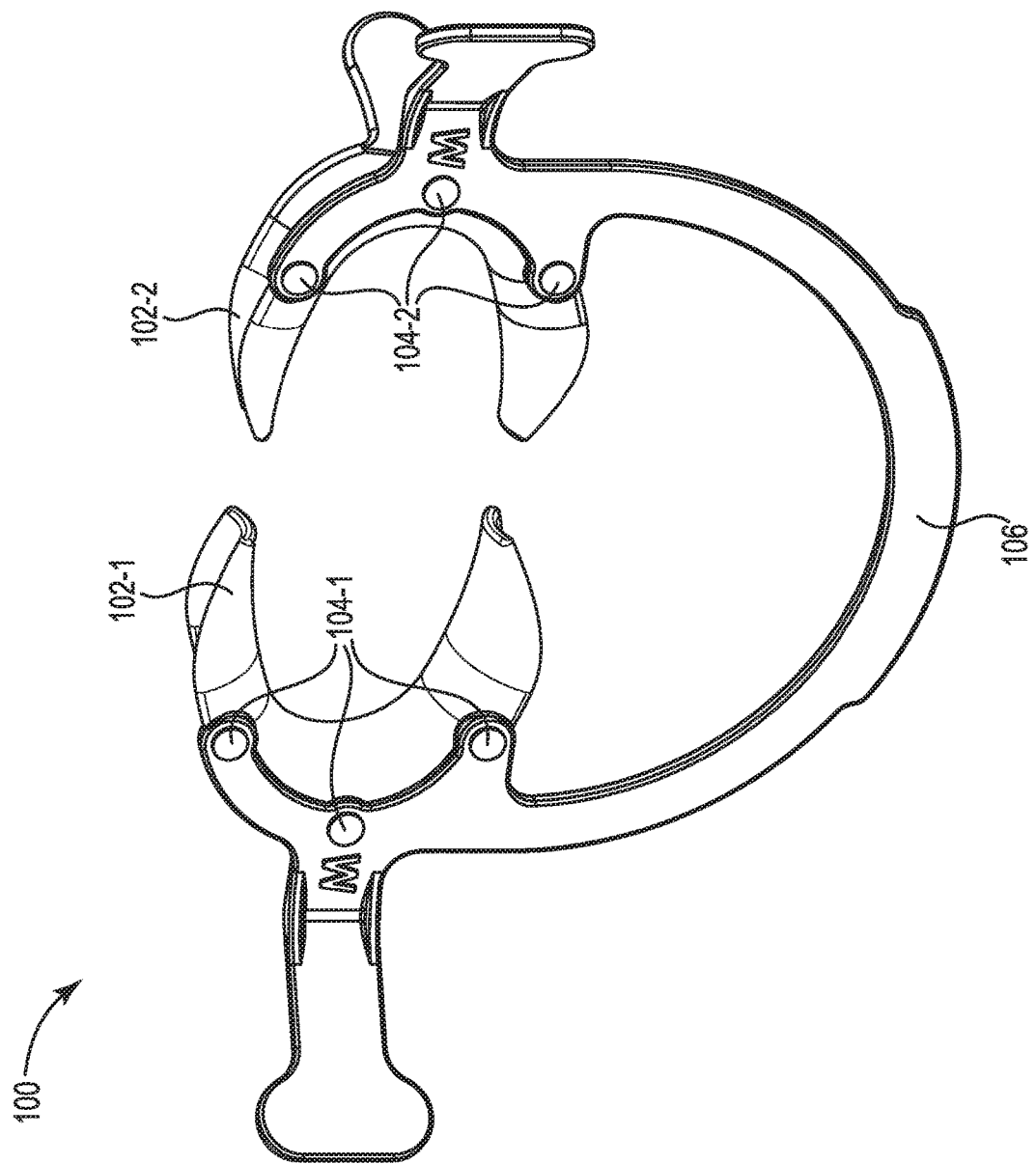
FIG. 1A illustrates a perspective view of a cheek retractor according to a number of embodiments of the present disclosure.

The present disclosure provides computing device readable medium, devices, and systems that utilize a cheek retractor and/or a mobile device holder for case assessment and/or dental treatments. Such solutions may simplify taking images of teeth of patients and/or prospective patients. Further, the images may include more consistent distances and/or angles from patients' teeth, allowing for more accurate scaling and rendering than images with inconsistent distances and/or angles from patients' teeth. The images can be more useful for progress tracking for current patients and/or determining whether various dental treatments will work on prospective patients.

In the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1A, and a similar element may be referenced as 204 in FIG. 2.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

FIG. 1A illustrates a perspective view of a cheek retractor according to a number of embodiments of the present disclosure. Cheek retractor 100 can include first lip holder 102-1, second lip holder 102-2, first imaging markers 104-1, second imaging markers 104-2, and bridge 106.

First lip holder 102-1 and second lip holder 102-2 can be shaped to fit into a user's mouth. As used herein, a user can include a patient and/or a prospective patient. The first lip holder 102-1 and second lip holder 102-2 can be of a "C" shape such that the first lip holder 102-1 and second lip holder 102-2 can follow the contour of the user's mouth and lips. The first lip holder 102-1 and second lip holder 102-2 can include a trough to receive the lips of the user. When inserted into the mouth of the user, the first lip holder 102-1 and second lip holder 102-2 are configured to hold the cheek of the user away from the user's mouth to expose the teeth of the user.

Cheek retractor 100 can include a bridge 106. Bridge 106 can connect the first lip holder 102-1 and second lip holder 102-2. Bridge 106 can be shaped to provide force to hold the cheek of the user away from the mouth of the user to expose the teeth of the user.

The first lip holder 102-1, second lip holder 102-2, and bridge 106 can be manufactured from material such as a plastic or other composite to provide the required force to hold the cheek of the user away from the user's mouth to expose the teeth of the user. The material can withstand sterilization techniques, including cold sterilization methods. The first lip holder 102-1, second lip holder 102-2, and bridge 106 can be manufactured from a material that is biocompatible such that it is not irritating to the user's oral mucosa and skin when inserted into the mouth of the user.

Cheek retractor 100 can be manufactured, in some examples, by downloading a computer-aided design (CAD) virtual model to a rapid prototyping process, such as, for example, a computer-aided manufacturing (CAM) milling, stereolithography, and/or photolithography process. In some examples, cheek retractor 100 can be manufactured via overmolding, injection molding, a rapid prototyping machine or direct fabrication device, such as a SLA or 3D printing machine, to form and/or create cheek retractor 100, among other manufacturing techniques and/or processes.

The first lip holder 102-1 can include first imaging markers 104-1. Each of the first imaging markers 104-1 can be located a predefined distance from the remaining first imaging markers 104-1. For example, as shown in FIG. 1A, the top imaging marker of the first imaging markers 104-1 can be located 2.3 centimeters (cm) from the middle imaging marker of the first imaging markers 104-1, and the middle imaging marker of the first imaging markers 104-1 can be located 2.3 cm from the bottom imaging marker of the first imaging markers 104-1, although embodiments of the present disclosure are not limited to the imaging markers being located 2.3 cm from each other. The top imaging marker of the first imaging markers 104-1 can be located 3.7 cm from the bottom imaging marker of the first imaging markers 104-1, although embodiments of the present disclosure are not limited to the top and the bottom imaging markers being located 3.7 cm from each other.

The second lip holder 102-2 can include second imaging markers 104-2. Each of the second imaging markers 104-2 can be located a predefined distance from the remaining second imaging markers 104-2. For example, as shown in FIG. 1A, the top imaging marker of the second imaging markers 104-2 can be located 2.3 centimeters (cm) from the middle imaging marker of the second imaging markers 104-2, and the middle imaging marker of the second imaging markers 104-2 can be located 2.3 cm from the bottom imaging marker of the second imaging markers 104-2, although embodiments of the present disclosure are not limited to the imaging markers being located 2.3 cm from each other. The top imaging marker of the second imaging markers 104-2 can be located 3.7 cm from the bottom imaging marker of the second imaging markers 104-2, although embodiments of the present disclosure are not limited to the top and the bottom imaging markers being located 3.7 cm from each other.

The first imaging markers 104-1 and the second imaging markers 104-2 (referred to collectively as imaging markers 104) can be a predetermined size and configured to determine the scale of the teeth of the user. For example, a computing device can receive images of the teeth of the user exposed by cheek retractor 100, where the images include the first imaging markers 104-1 and the second imaging markers 104-2. The computing device can utilize the predetermined size of the first imaging markers 104-1 and the second imaging markers 104-2 and the predefined distances between them to determine a scale of the teeth of the user by equating the predefined distances between the first imaging markers 104-1 and the second imaging markers 104-2 to a number of pixels in the images, as will be further described herein with respect to FIG. 6.

In some embodiments, the first imaging markers 104-1 and the second imaging markers 104-2 can be on a same plane with respect to each other in three-dimensional (3D) space. For example, the first imaging markers 104-1 can be in a same plane, and the second imaging markers 104-2 can be in a same plane. The plane of the first imaging markers 104-1 and the plane of the second imaging markers 104-1 can be the same plane or can be different planes. In some embodiments, the first imaging markers 104-1 can be located at different angles with respect to each other, and the second imaging markers 104-2 can be located at different angles with respect to each other. The scale of the teeth of the user may be determined using the predefined distances of the imaging markers 104, the predetermined size of the imaging markers 104, the planes of the imaging markers 104, and/or the angles of imaging markers 104. The scale of the teeth may be determined in 3D space using, for example, an X, Y, and/or Z coordinate system.

The first imaging markers 104-1 and the second imaging markers 104-2 can be a paper material, although embodiments of the present disclosure are not limited to a paper material. In some examples, the first imaging markers 104-1 and the second imaging markers 104-2 can be included on cheek retractor 100 during an overmolding and/or injection molding process, among other manufacturing techniques and/or processes. In some examples, the first imaging markers 104-1 and the second imaging markers 104-2 can be included on cheek retractor 100 by being stuck on (e.g., imaging markers 104 can be stickers placed on cheek retractor 100).

As shown in FIG. 1A, first lip holder 102-1 includes three first imaging markers 104-1 and second lip holder 102-2 includes three second imaging markers 104-2. Having three imaging markers can provide a more accurate scale of the user's teeth as compared to using less than three imaging markers, as well as providing more accurate reference points when combining multiple images of the user's teeth than using less than three imaging markers, as will be further described herein with respect to FIG. 6.

Although described herein and shown in FIG. 1A as first lip holder 102-1 including three imaging markers and second lip holder 102-2 including three imaging markers, embodiments of the present disclosure are not so limited. For example, first lip holder 102-1 can include more than three imaging markers, and second lip holder 102-2 can include more than three imaging markers.

The first imaging markers 104-1 and the second imaging markers 104-2 can be colored, and include one color or multiple colors. In some examples, cheek retractor 100 can be colored (e.g., green), and the first imaging markers 104-1 and the second imaging markers 104-2 can be a single solid color (e.g., orange). In some examples, cheek retractor 100 can be transparent, and the first imaging markers 104-1 and the second imaging markers 104-2 can be a multiple colors (e.g., orange with a secondary blue or green circle). Utilizing orange and/or orange with secondary blue or green imaging markers can provide a color contrast in images relative to other colored imaging markers, although embodiments of the present disclosure are not limited to orange and/or orange/blue/green color combinations.

The first imaging markers 104-1 and the second imaging markers 104-2 can be circular. However, embodiments of the present disclosure are not limited to circular imaging markers. For example, the first imaging markers 104-1 and the second imaging markers 104-2 can be other shapes, including squares, rectangles, etc., as well as other irregular shapes (e.g., a circle with a portion of the circle removed), etc.

Cheek retractor 100 can be used by a user to take images (e.g., photograph(s) and/or video) of the user's teeth. The images can include the first imaging markers 104-1 and the second imaging markers 104-2 which may be used to determine a scale of the user's teeth. Utilizing the images of and the scale of the user's teeth, a computing device may generate a model of the user's teeth, as will be further described herein with respect to FIG. 6. The model may be a two-dimensional (2D) and/or a three-dimensional (3D) model.

The model may be used, in some examples, to determine whether a user's teeth are suitable for a particular dental procedure (e.g., case assessment). For example, a treatment professional can review the model to determine a severity of a patient's malocclusion (e.g., mild, moderate, etc.), a type of dental procedure and associated dental appliances that would be suitable for fixing the particular malocclusion, and/or an amount of time needed to fix the particular malocclusion, among other factors.

The model may be used, in some examples, to track the progress of an ongoing dental procedure for a particular user. The model generated from the images can be compared to a predefined model of the user's teeth to track the progress of the ongoing dental procedure. For example, a treatment professional can review the model and compare it to a predefined model that may have been generated at the onset of the dental procedure to determine whether the dental procedure is proceeding as anticipated. The treatment professional can continue the dental procedure for the user if the dental procedure is proceeding as anticipated. Additionally, the treatment professional may make alterations to the dental procedure in the event the dental procedure is not proceeding as anticipated.

The cheek retractor including the imaging markers can assist in generating an accurate model of the user's teeth. The model can allow a treatment professional to determine whether a user's teeth are suitable for a particular dental procedure and/or to track an ongoing dental procedure. The treatment professional can utilize the model to help make this determination without the user having to make a time consuming visit the treatment professional, saving both the user and the treatment professional time and money.

Figure 1B:
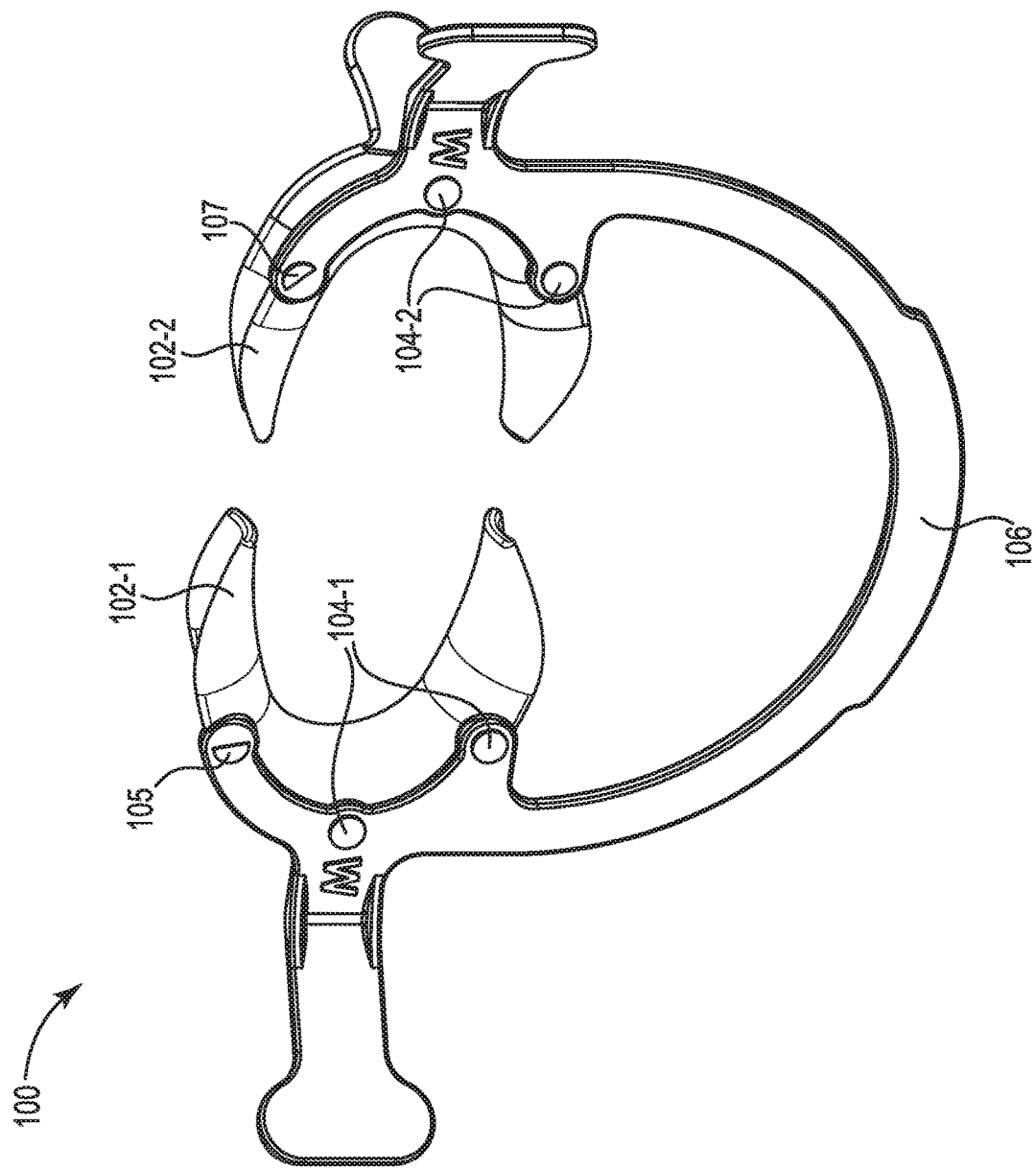
FIG. 1B illustrates a perspective view of a cheek retractor according to a number of embodiments of the present disclosure.

FIG. 1B illustrates a perspective view of a cheek retractor according to a number of embodiments of the present disclosure. As previously described in connection with FIG. 1A, cheek retractor 100 can include first lip holder 102-1, second lip holder 102-2, first imaging markers 104-1, second imaging markers 104-2, and bridge 106. Cheek retractor 100 can further include sizing imaging marker 105 and sizing imaging marker 107.

The first lip holder 102-1 can include first imaging markers 104-1 and sizing imaging marker 105. Each of the first imaging markers 104-1 and sizing imaging marker 105 can be located a predefined distance from each other. For example, as shown in FIG. 1B, sizing imaging marker 105 can be located 2.3 centimeters (cm) from the middle-left imaging marker of the first imaging markers 104-1, and the middle-left imaging marker of the first imaging markers 104-1 can be located 2.3 cm from the bottom imaging marker of the first imaging markers 104-1, although embodiments of the present disclosure are not limited to the imaging markers being located 2.3 cm from each other. Sizing imaging marker 105 can be located 3.7 cm from the bottom imaging marker of the first imaging markers 104-1, although embodiments of the present disclosure are not limited to sizing imaging marker 105 and the bottom imaging marker of the first imaging markers 104-1 being located 3.7 cm from each other.

The second lip holder 102-2 can include second imaging markers 104-2 and sizing imaging marker 107. Each of the second imaging markers 104-2 and sizing imaging marker 107 can be located a predefined distance from the remaining second imaging markers 104-2. For example, as shown in FIG. 1B, sizing imaging marker 107 can be located 2.3 centimeters (cm) from the middle-right imaging marker of the second imaging markers 104-2, and the middle-right imaging marker of the second imaging markers 104-2 can be located 2.3 cm from the bottom imaging marker of the second imaging markers 104-2, although embodiments of the present disclosure are not limited to the imaging markers being located 2.3 cm from each other. Sizing imaging marker 107 can be located 3.7 cm from the bottom imaging marker of the second imaging markers 104-2, although embodiments of the present disclosure are not limited to the sizing imaging marker 107 and the bottom imaging marker of the second imaging markers 104-2 being located 3.7 cm from each other.

As previously described in connection with FIG. 1A, first imaging markers 104-1 and second imaging markers 104-2, as well as sizing imaging marker 105 and sizing imaging marker 107 can be a predetermined size and used to determine the scale of the teeth of the user. For example, a computing device can receive images of the teeth of the user exposed by cheek retractor 100, where the images include the first imaging markers 104-1, sizing imaging marker 105, the second imaging markers 104-2, and sizing imaging marker 107. The computing device can utilize the predetermined size of first imaging markers 104-1, sizing imaging marker 105, the second imaging markers 104-2, and sizing imaging marker 107 and the predefined distances between them to determine a scale of the teeth of the user by equating the predefined distances between first imaging markers 104-1, sizing imaging marker 105, the second imaging markers 104-2, and sizing imaging marker 107 to a number of pixels in the images, as will be further described herein with respect to FIG. 6.

Sizing imaging marker 105 and sizing imaging marker 107 can be used to determine a size of cheek retractor 100. The size of cheek retractor 100 can correspond to a size of a patient's mouth. For example, a first patient may have a mouth size corresponding to a large sized cheek retractor 100, while a second patient may have a mouth size corresponding to a medium sized cheek retractor 100. Cheek retractor 100 sizes may vary from small, medium, large, extra-large, etc. Additionally, cheek retractor 100 sizes may include sizes from less than small to larger than extra-large.

Sizing imaging marker 105 and sizing imaging marker 107 can include shapes and/or orientations that correspond to the size of cheek retractor 100. For example, as illustrated in FIG. 1B, sizing imaging marker 105 is a half-circle shape, where the half-circle portion of the imaging marker is oriented vertically and on a left side of a sizing imaging marker location on cheek retractor 100 as viewed from the perspective illustrated in FIG. 1B. The left and vertically oriented sizing imaging marker 105 can correspond to a medium sized cheek retractor 100. As another example, as illustrated in FIG. 1B, sizing imaging marker 107 is a half circle shape, where the half-circle portion of the imaging marker is oriented horizontally and on a top side of a sizing imaging marker location on cheek retractor 100 as viewed from the perspective illustrated in FIG. 1B. The top and horizontally oriented sizing imaging marker 107 can correspond to a large sized cheek retractor 100.

In some examples, a combination of the orientation and placement of sizing imaging markers 105, 107 can correspond to the size of cheek retractor 100. For example, the left and vertically oriented sizing imaging marker 105 and the top and horizontally oriented sizing imaging marker 107 can correspond to a medium sized cheek retractor 100. As another example, a right and vertically oriented sizing imaging marker 105 and a bottom and horizontally oriented sizing imaging marker 107 can correspond to a large sized cheek retractor 100, among other combinations of the orientation and placement of sizing imaging markers 105, 107.

Although sizing imaging markers 105, 107 are illustrated in FIG. 1B and described above as being left and vertically oriented and top and horizontally oriented, respectively, embodiments of the present disclosure are not so limited. In some examples, sizing imaging marker 105 can be right and vertically oriented, top and horizontally oriented, bottom and horizontally oriented, oriented at an angle between 0 and 360°, etc. In some examples, sizing imaging marker 107 can be bottom and horizontally oriented, left and vertically oriented, right and vertically oriented, oriented at an angle between 0 and 360°, etc. In some examples, sizing imaging markers 105, 107 can be shapes other than a half-circle. For example, sizing imaging markers 105, 107 can be semi-circles (e.g., less than and/or greater than a half-circle shape), squares, rectangles, other irregular shapes (e.g., a circle with a portion of the circle removed), etc.

Sizing imaging markers 105, 107 can be a paper material, can be included on cheek retractor 100 during an overmolding and/or injection molding process, and/or can be stickers, similar to first imaging markers 104-1 and second imaging markers 104-2, as previously described in connection with FIG. 1A. Sizing imaging markers 105, 107 can be colored, and can include one color or multiple colors, similar to first imaging markers 104-1 and second imaging markers 104-2, as previously described in connection with FIG. 1A.

As previously described in connection with FIG. 1A, cheek retractor 100 can be used by a user to take images (e.g., photograph(s) and/or video) of the user's teeth. The images can include the first imaging markers 104-1 and the second imaging markers 104-2, as well as sizing imaging markers 105, 107, which may be used to determine a scale of the user's teeth and a size of cheek retractor 100. Utilizing the images of and the scale of the user's teeth and the size of cheek retractor 100, a computing device may generate a model of the user's teeth, as will be further described herein with respect to FIG. 6. The model may be a two-dimensional (2D) and/or a three-dimensional (3D) model. The model may be used to determine whether a user's teeth are suitable for a particular dental procedure, to track progress of an ongoing dental procedure, and/or assist in generating an accurate model of the user's teeth, among other uses, as previously described in connection with FIG. 1A.

Figure 1C:
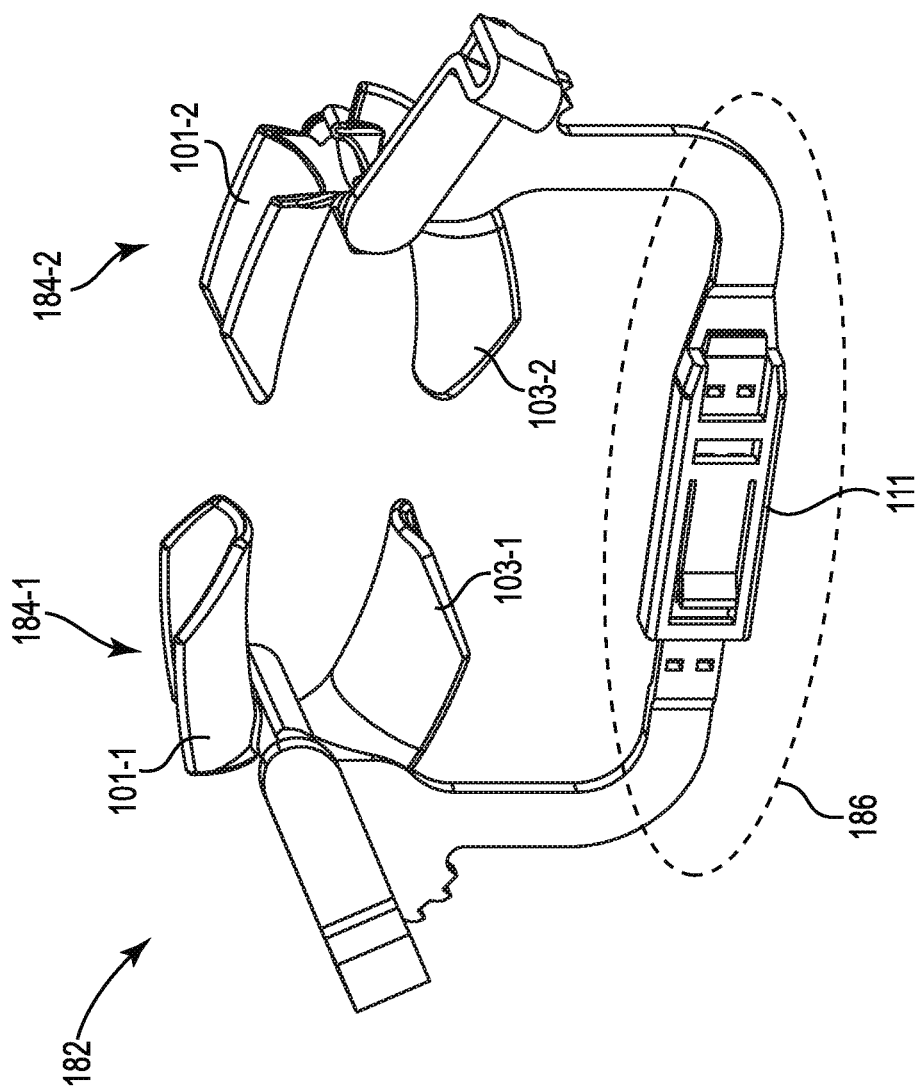
FIG. 1O illustrates a perspective view of an adjustable cheek retractor according to a number of embodiments of the present disclosure.
FIG. 1D illustrates perspective views of a first portion and a second portion of an adjustable cheek retractor according to a number of embodiments of the present disclosure.
FIG. 1E illustrates perspective views of a first portion of an adjustable cheek retractor, an upper portion of a lip holder and a bottom portion of a lip holder of an adjustable cheek retractor according to a number of embodiments of the present disclosure.
FIG. 1F illustrates perspective views of an adjustable cheek retractor according to a number of embodiments of the present disclosure.
FIG. 1G illustrates perspective views of an adjustable cheek retractor having a pulled apart rotational ratcheting mechanism according to a number of embodiments of the present disclosure.
FIG. 1H illustrates perspective views of an adjustable cheek retractor according to a number of embodiments of the present disclosure.

FIG. 1C illustrates a perspective view of an adjustable cheek retractor 182 according to a number of embodiments of the present disclosure. Adjustable cheek retractor 182 can include first lip holder 184-1, second lip holder 184-2, and bridge 186. First lip holder 184-1 can include upper portion 101-1 and bottom portion 103-1. Second lip holder 184-2 can include upper portion 101-2 and bottom portion 103-2.

First lip holder 184-1 and second lip holder 184-2 can be shaped to fit into a user's mouth. For example, the upper portion 101-1 and the bottom portion 103-1 of the first lip holder 184-1 can be of a "C" shape such that the upper portion 101-1 and the bottom portion 103-1 can follow the contour of the user's mouth and lips. Similarly, the upper portion 101-2 and the bottom portion 103-2 of the second lip holder 184-2 can be of a "C" shape such that the upper portion 101-2 and the bottom portion 103-2 can follow the contour of the user's mouth and lips.

The first lip holder 184-1 and the second lip holder 184-2 can be height adjustable. For example, the upper portion 101-1 can be connected to the bottom portion 103-1 of the first lip holder 184-1 at a hinge, the upper portion 101-2 can be connected to the bottom portion 103-2 of the second lip holder 184-2 at a hinge. The first lip holder 184-1 can be height adjustable about the hinge of first lip holder 184-1, and the second lip holder 184-2 can be height adjustable about the hinge of second lip holder 184-2, as is further described in connection with FIG. 1E.

Adjustable cheek retractor 182 can include a bridge 186. Bridge 186 can include a latch mechanism 111. The first lip holder 184-1 and the second lip holder 184-2 can be connected via the latch mechanism 111 of the bridge 186.

The width between the first lip holder 184-1 and the second lip holder 184-2 can be adjustable. For example, a first user may have a larger mouth than a second user; the width between first lip holder 184-1 and second lip holder 184-2 can be made to be larger in order for the first user to utilize adjustable cheek retractor 182 to hold a cheek away from the mouth of the first user in order to expose the teeth of the first user. The width between the first lip holder 184-1 and the second lip holder 184-2 can be adjustable via the latch mechanism 111, as is further described in connection with FIG. 1D.

Although not shown in FIG. 1C for clarity and so as not to obscure embodiments of the present disclosure, in some examples, the adjustable cheek retractor 182 can include imaging markers. For example, the first lip holder 184-1 can include first sizing imaging markers and the second lip holder 184-2 can include second sizing imaging markers. The imaging markers on the first lip holder 184-1 can be included on the upper portion 101-1, the bottom portion 103-1, and/or any combination thereof. Similarly, the imaging markers on the second lip holder 184-2 can be included on the upper portion 101-2, the bottom portion 103-2, and/or any combination thereof. The sizing imaging markers can correspond to a size of the adjustable cheek retractor 182.

Figure 1D:
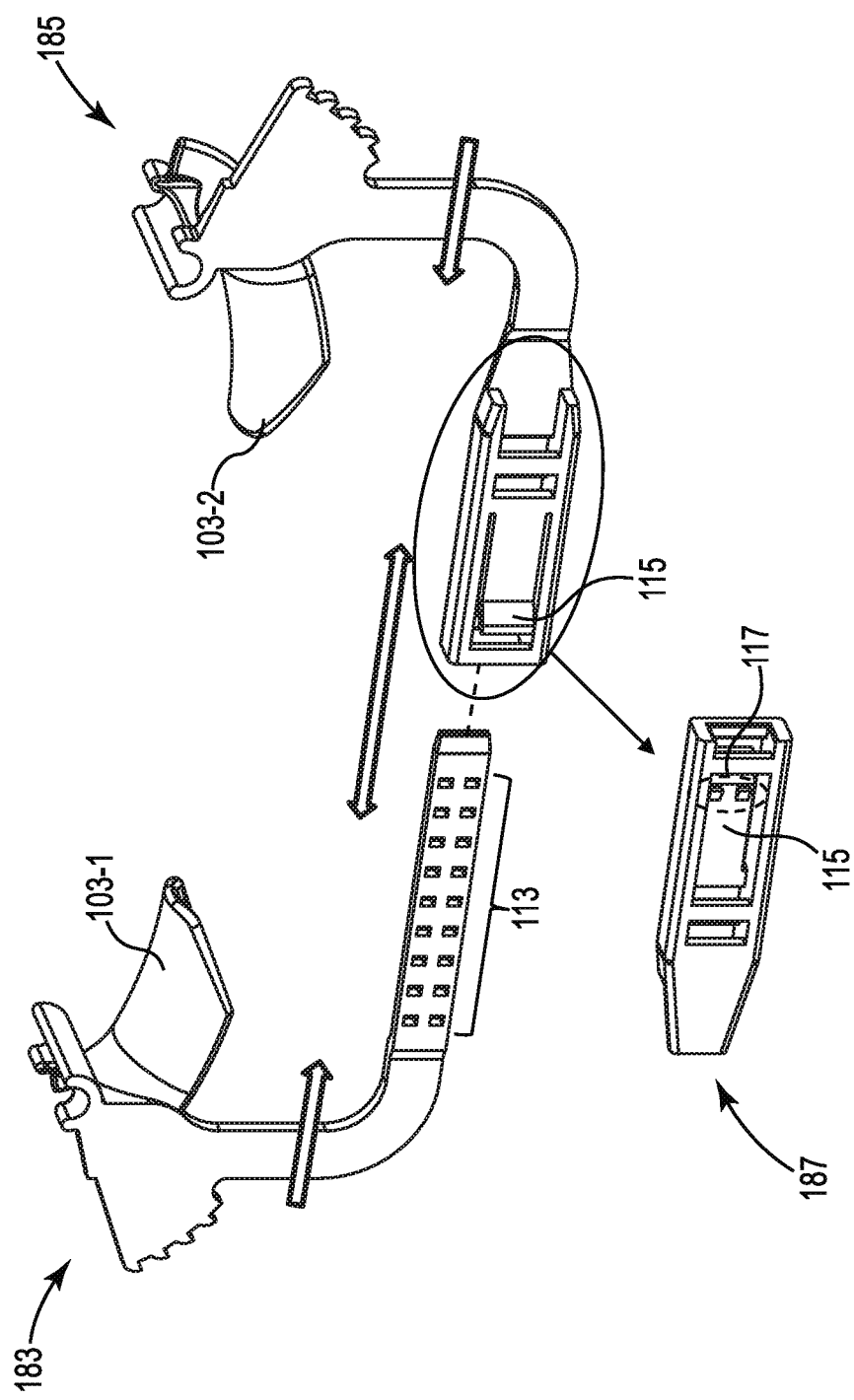

FIG. 1D illustrates perspective views of a first portion 183 and a second portion 185 of an adjustable cheek retractor according to a number of embodiments of the present disclosure. The adjustable cheek retractor can include bottom portion 103-1 of the first lip holder and bottom portion 103-2 of the second lip holder, plurality of engagement apertures 113, latch 115, and engagement teeth 117 as illustrated in reverse view 187 of latch 115.

As previously described in connection with FIG. 10, the adjustable cheek retractor can include a bridge connecting the first lip holder and the second lip holder. The bridge can include a latch mechanism. As illustrated in FIG. 1D, the latch mechanism can include a plurality of engagement apertures 113 and a latch 115.

An aperture can, for example, refer to an opening in the bridge. The plurality of engagement apertures 113 can engage with engagement teeth 117. For example, the width between first portion 183 and the second portion 185 of the adjustable cheek retractor can be adjustable via the plurality of engagement structures 113 and the latch 115 having the engagement teeth 117, as is further described herein.

The engagement teeth 117 can engage particular engagement apertures of the plurality of engagement apertures 113. An engagement tooth can, for example, refer to a projecting member that can engage a corresponding aperture. As illustrated in FIG. 1D, engagement teeth 117 can engage particular engagement apertures of the plurality of engagement apertures 113. For instance, engagement teeth 117 can engage a top particular engagement aperture and a bottom particular aperture of the plurality of engagement apertures 113 (e.g., as oriented in FIG. 1D) such that the first portion 183 and the second portion 185 of the adjustable cheek retractor are at a fixed width relative to each other, where the fixed width is based on the particular top and bottom apertures engaged by the engagement teeth 117.

The width between the first portion 183 and the second portion 185 of the adjustable cheek retractor can be adjusted by adjusting the particular engagement apertures the engagement teeth 117 engage. For example, the width can be increased or decreased by engagement teeth 117 engaging different particular engagement apertures of the plurality of engagement apertures 113.

As illustrated in FIG. 1D, the engagement teeth 117 can be angled. The angled engagement teeth 117 can allow for the width between the first portion 183 and the second portion 185 of the adjustable cheek retractor to be adjusted to be larger without lifting latch 115. For example, the angle of engagement teeth 117 can be oriented such that the first portion 183 and the second portion 185 can be pulled apart to increase the width between the first portion 183 and the second portion 185 without lifting latch 115. The angle can allow the engagement teeth 117 to slide to different particular apertures of the plurality of engagement apertures 113 to increase the width.

In an example in which the adjustable cheek retractor is placed in a patient's mouth, allowing the width of the adjustable cheek retractor to be increased without lifting the latch 115 can allow for a user (e.g., the patient, treatment professional, etc.) to increase the width against an opposing force generated by the patient's cheeks and mouth.

The width between the first portion 183 and the second portion 185 of the adjustable cheek retractor can be adjusted to be smaller by lifting latch 115 to allow the engagement teeth 117 to slide to engage different particular engagement structures. For instance, the angle of the engagement teeth 117 will not allow for movement of the first portion 183 and the second portion 185 of the adjustable cheek retractor without lifting the latch 115. Therefore, a user (e.g., the patient, treatment professional, etc.) can lift the latch 115 to allow for movement of the first portion 183 and the second portion 185 to narrow the width between the first portion 183 and the second portion 185 of the adjustable cheek retractor. At the desired width, the user can release the latch 115, allowing for engagement teeth 117 to engage with particular engagement apertures of the plurality of engagement apertures 113.

FIG. 1E illustrates perspective views of a first portion 189 of an adjustable cheek retractor, an upper portion 101-1 of a lip holder 184-1 and a bottom portion 103-1 of a lip holder 184-1 of an adjustable cheek retractor according to a number of embodiments of the present disclosure.

The adjustable cheek retractor can include a first portion 189 having a first lip holder 184-1. The first lip holder 184-1 can include an upper portion 101-1 of the first lip holder 184-1 and a bottom portion 103-1 of the first lip holder 184-1.

The first lip holder 184-1 can be height adjustable. For example, the height between the upper portion 101-1 and the bottom portion 103-1 can be adjusted. The first lip holder 184-1 can be height adjustable about a hinge 121 of the first lip holder 184-1 via a ratcheting mechanism 119, as is further described herein.

Although not illustrated in FIG. 1E for clarity and so as not to obscure examples of the disclosure, the adjustable cheek retractor can include a second lip holder having an upper portion and a bottom portion. The second lip holder can be height adjustable about a hinge of the second lip holder via a ratcheting mechanism of the second lip holder, similar to the first lip holder 184-1.

The first lip holder 184-1 can include an upper portion 101-1. As illustrated by perspective view 191 in FIG. 1E, shows the upper portion 101-1 of the first lip holder 184-1. Upper portion 101-1 can include a barrel 123 and an adjustment tooth 127.

The first lip holder 184-1 can also include a bottom portion 101-2. As illustrated by perspective view 193 in FIG.

1E, shows the bottom portion 103-1 of the first lip holder 184-1. Bottom portion 103-1 can include a channel 125 and a plurality of ratcheting teeth 129.

As previously described above, the first lip holder 184-1 can include hinge 121. Hinge 121 can be comprised of the barrel 123 and channel 125. For example, barrel 123 can fit into channel 125 to form hinge 121. The barrel 123 can fit into channel 125 via an interference fit, and barrel 123 can rotate in channel 125. In other words, the barrel 123 can rotate in channel 125 to adjust the height of the first lip holder 184-1 by causing the upper portion 101-1 to rotate relative to the bottom portion of 103-1, as is further described herein.

Upper portion 101-1 can be connected to the bottom portion 103-1 via the ratcheting mechanism 119 and the hinge 121. The first lip holder 184-1 can be height adjustable via the ratcheting mechanism 119.

As previously described above, the upper portion 101-1 can include an adjustment tooth 127 and the bottom portion 101-3 can include a plurality of ratcheting teeth 129. The adjustment tooth 127 can engage a particular ratcheting tooth of the plurality of ratcheting teeth 129 to form the ratcheting mechanism 119. For example, adjustment tooth 127 can engage a particular ratcheting tooth such that the upper portion 101-1 and the bottom portion 103-1 are at a fixed height relative to each other, where the fixed height is based on the particular ratcheting tooth of the plurality of ratcheting teeth 129 engaged by the adjustment tooth 127.

The first lip holder 184-1 can be height adjustable by the adjustment tooth engaging a different ratcheting tooth of the plurality of ratcheting teeth 129. For example, the height can be increased or decreased by the adjustment tooth 127 engaging a different particular ratcheting tooth of the plurality of ratcheting teeth 129.

As illustrated in FIG. 1E, the plurality of ratcheting teeth 129 can be angled. Additionally, the adjustment tooth 127 can be angled. The angled plurality of ratcheting teeth 129 and the angled adjustment tooth 127 can allow for the height between the upper portion 101-1 and the bottom portion 103-1 to be adjusted to be larger without lifting adjustment tooth 127. For example, the angles of the plurality of ratcheting teeth 129 and the adjustment tooth 127 can be oriented such that the upper portion 101-1 and the bottom portion 103-1 can be rotated away from each other to increase the height between the upper portion 101-1 and the bottom portion 103-1 without lifting adjustment tooth 127. The angles of the plurality of ratcheting teeth 129 and the adjustment tooth 127 can allow the adjustment tooth 127 to slide to different particular ratcheting teeth of the plurality of ratcheting teeth 129 to increase the height.

In an example in which the adjustable cheek retractor is placed in a patient's mouth, allowing the height of the adjustable cheek retractor to be increased without lifting the adjustment tooth 127 can allow for a user (e.g., the patient, treatment professional, etc.) to increase the height against an opposing force generated by the patient's cheeks and mouth.

The height between the upper portion 101-1 and the bottom portion 103-1 can be adjusted to be smaller by lifting adjustment tooth 127 to allow the upper portion 101-1 to rotate. For instance, the angle of the adjustment tooth 127 and the plurality of ratcheting teeth 129 will not allow for movement of the upper portion 101-1 relative to the bottom portion 103-1 without lifting adjustment tooth 127 clear of the plurality of ratcheting teeth 129. Therefore, a user (e.g., the patient, treatment professional, etc.) can lift adjustment tooth 127 to allow for the upper portion 101-1 to rotate towards the bottom portion 103-1 to decrease the height between the upper portion 101-1 and the bottom portion 103-1. At the desired height between the upper portion 101-1 and the bottom portion 103-1, the user can release the adjustment tooth 127, allowing for the adjustment tooth 127 to engage a particular ratcheting tooth of the plurality of ratcheting teeth 129.

Although not shown in FIG. 1E for clarity and so as not to obscure embodiments of the present disclosure, the second lip holder (e.g., second lip holder 184-2) can include an upper portion, a bottom portion, a hinge, and a ratcheting mechanism. The second lip holder can be height adjustable similar to first lip holder 184-1.

FIG. 1F illustrates perspective views 194 of an adjustable cheek retractor according to a number of embodiments of the present disclosure. The adjustable cheek retractor can include first lip holder 184-1, second lip holder 184-2, and bridge 186. Bridge 186 can include rotational ratcheting mechanism 199.

As illustrated in FIG. 1F, the adjustable cheek retractor can include bridge 186. Bridge 186 can include a rotational ratcheting mechanism 199. The first lip holder 184-1 and the second lip holder 184-2 can be connected via the rotational ratcheting mechanism 199 of bridge 186.

The width between the first lip holder 184-1 and the second lip holder 184-2 can be adjustable. For example, a first user may have a larger mouth than a second user; the width between first lip holder 184-1 and second lip holder 184-2 can be made to be larger in order for the first user to utilize the adjustable cheek retractor to hold a cheek away from the mouth of the first user in order to expose the teeth of the first user. The width between the first lip holder 184-1 and the second lip holder 184-2 can be adjustable via the rotational ratcheting mechanism 199.

The rotational ratcheting mechanism 199 can include an adjustment tooth 195 and a plurality of ratcheting teeth 197. The adjustment tooth 195 can engage a particular ratcheting tooth of the plurality of ratcheting teeth 197. For example, adjustment tooth 195 can engage a particular ratcheting tooth such that first lip holder 184-1 and second lip holder 184-2 are at a fixed width relative to each other, where the fixed width is based on the particular ratcheting tooth of the plurality of ratcheting teeth 197 engaged by the adjustment tooth 195.

The first lip holder 184-1 and the second lip holder 184-2 can be width adjustable by the adjustment tooth 195 engaging a different ratcheting tooth of the plurality of ratcheting teeth 197. For example, the width can be increased or decreased by the adjustment tooth 195 engaging a different particular ratcheting tooth of the plurality of ratcheting teeth 197.

As illustrated in FIG. 1F, the plurality of ratcheting teeth 197 can be curved. Additionally, the adjustment tooth 195 can be angled. The curved plurality of ratcheting teeth 197 and the angled adjustment tooth 195 can allow for the width between the first lip holder 184-1 and the second lip holder 184-2 to be adjusted to be larger without lifting adjustment tooth 195. For example, the curves of the plurality of ratcheting teeth 197 and the angle of the adjustment tooth 195 can be oriented such that the first lip holder 184-1 and the second lip holder 184-2 can be rotated away from each other to increase the width between the first lip holder 184-1 and the second lip holder 184-2 without lifting adjustment tooth 195. The curves of the plurality of ratcheting teeth 197 and the angle of the adjustment tooth 195 can allow the adjustment tooth 195 to slide to different particular ratcheting teeth of the plurality of ratcheting teeth 197 to increase the width.

In an example in which the adjustable cheek retractor is placed in a patient's mouth, allowing the width of the adjustable cheek retractor to be increased without lifting the adjustment tooth 195 can allow for a user (e.g., the patient, treatment professional, etc.) to increase the width against an opposing force generated by the patient's cheeks and mouth.

The width between the first lip holder 184-1 and the second lip holder 184-2 can be adjusted to be smaller. For example, the width between the first lip holder 184-1 and the second lip holder 184-2 can be adjusted to be smaller by pulling apart the cheek retractor at the rotational ratcheting mechanism 199, as is further described herein with respect to FIG. 1G.

Figure 1G:
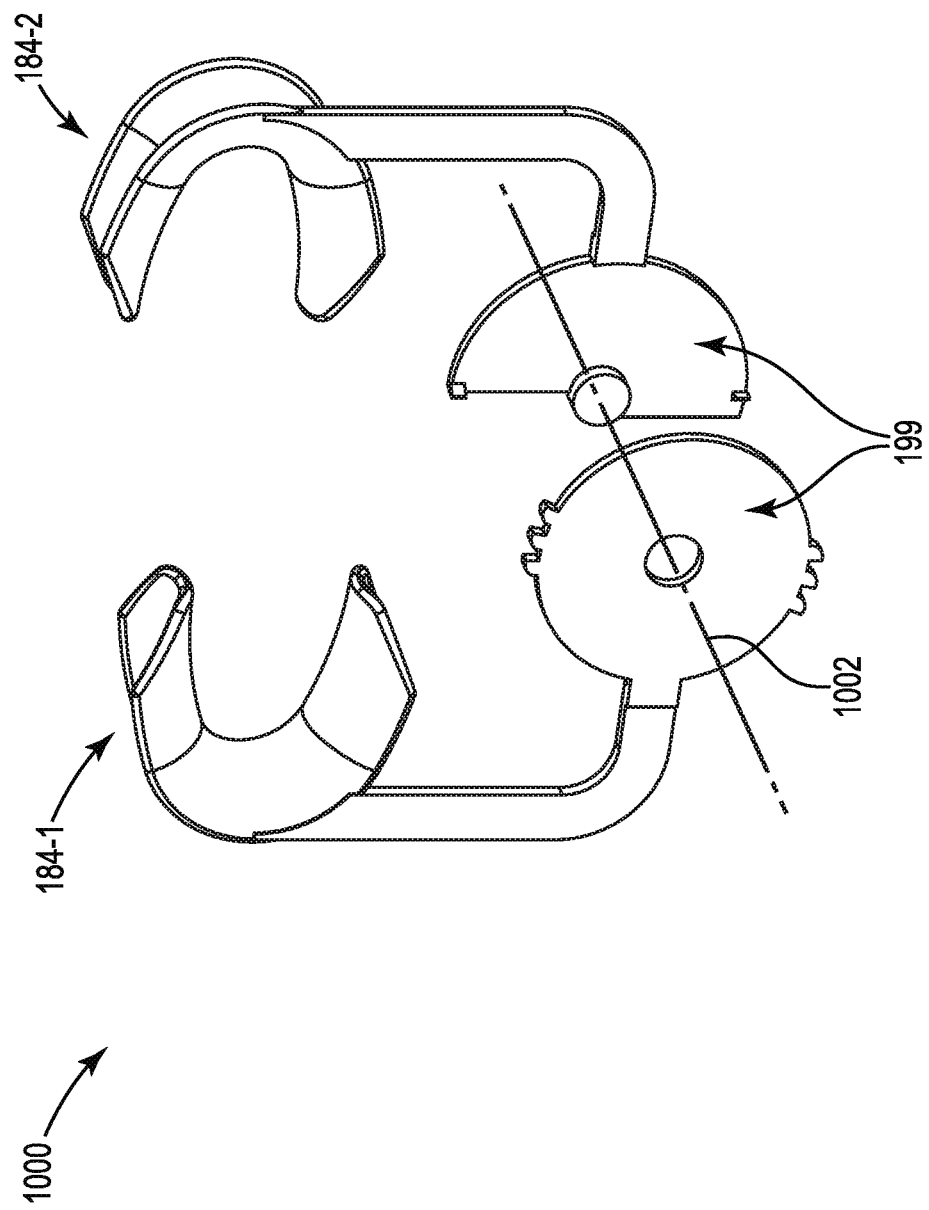

FIG. 1G illustrates perspective views 1000 of an adjustable cheek retractor having a pulled apart rotational ratcheting mechanism 199 according to a number of embodiments of the present disclosure. The adjustable cheek retractor can include first lip holder 184-1, second lip holder 184-2, and rotational ratcheting mechanism 199 aligned via central axis 1002.

The width between the first lip holder 184-1 and the second lip holder 184-2 can be adjusted to be smaller by pulling apart the rotational ratcheting mechanism 199. For example, rotational ratcheting mechanism 199, as illustrated in FIG. 1G, can be connected via a protrusion and an aperture aligned via central axis 1002. In some examples, protrusion can fit into the aperture via a mechanical fit and/or interference fit.

In order to adjust the width to be smaller, the rotational ratcheting mechanism 199 has to be pulled apart, as the angle of the adjustment tooth and the curves of the plurality of ratcheting teeth (e.g., adjustment tooth 195 and plurality of ratcheting teeth 197, previously described in connection with FIG. 1F) will not allow for movement of the first lip holder 184-1 relative to the second lip holder 184-2 without pulling apart the rotational ratcheting mechanism 199 so that the adjustment tooth is clear of the plurality of ratcheting teeth.

Therefore, a user (e.g., the patient, treatment professional, etc.) can pull apart rotational ratcheting mechanism 199 to allow for the first lip holder 184-1 and the second lip holder 184-2 to rotate towards each other to decrease the width between the first lip holder 184-1 and the second lip holder 184-2. At the desired width between the first lip holder 184-1 and the second lip holder 184-2, the user can connect the rotational ratcheting mechanism via central axis 1002, allowing for the adjustment tooth to engage a particular ratcheting tooth of the plurality of ratcheting teeth.

Figure 1H:
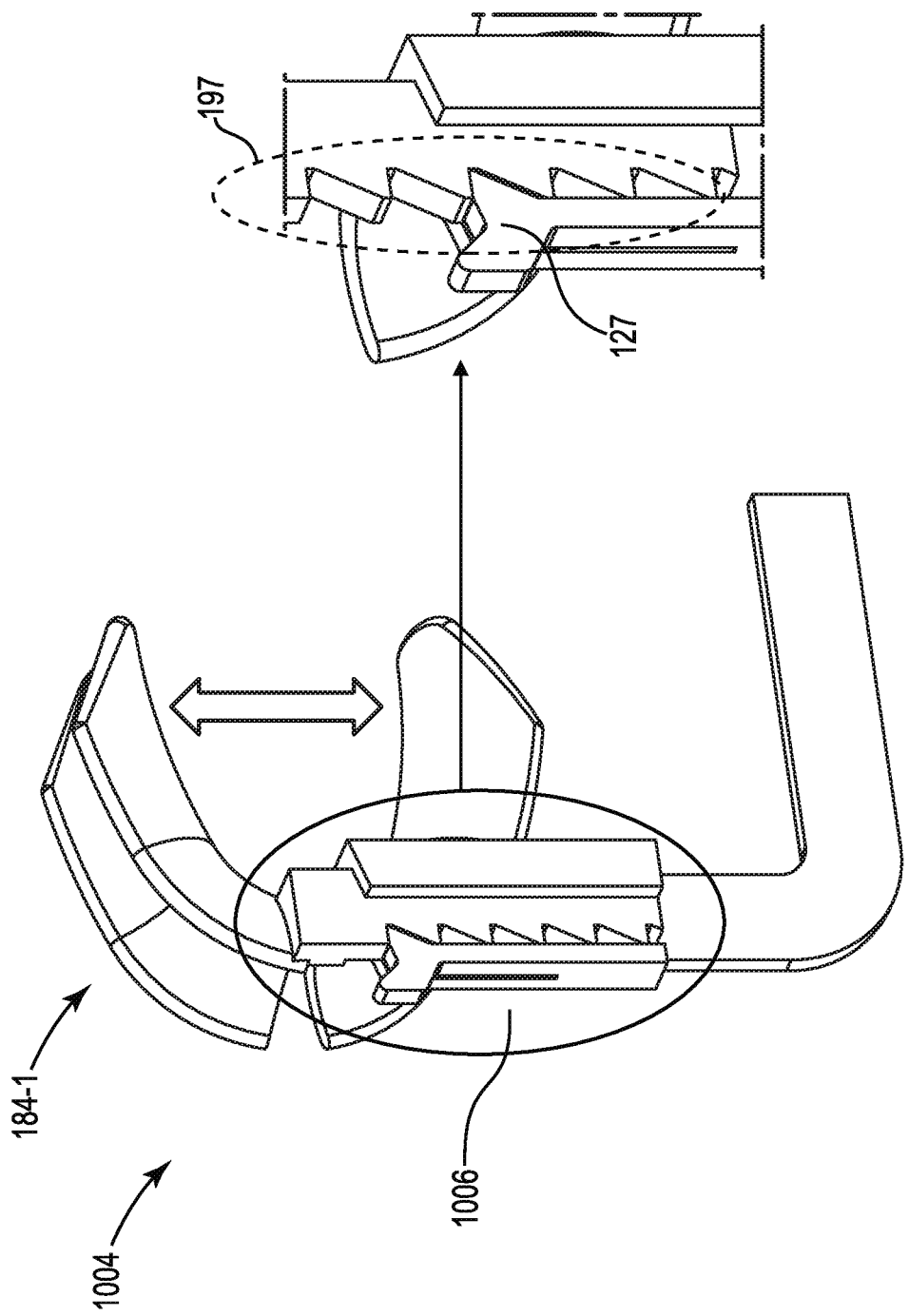

FIG. 1H illustrates perspective views 1004 of an adjustable cheek retractor according to a number of embodiments of the present disclosure. The adjustable cheek retractor can include a first lip holder 184-1 and a linear ratcheting mechanism 1006. The linear ratcheting mechanism 1006 can include an adjustment tooth 195 and a plurality of ratcheting teeth 197.

The first lip holder 184-1 can be height adjustable. For example, the height between the upper portion and a bottom portion of first lip holder 184-1 can be adjusted. The first lip holder 184-1 can be height adjustable via a linear ratcheting mechanism 1006, as is further described herein.

Although not illustrated in FIG. 1H for clarity and so as not to obscure examples of the disclosure, the adjustable cheek retractor can include a second lip holder having an upper portion and a bottom portion. The second lip holder can be height adjustable about a linear ratcheting mechanism of the second lip holder, similar to the first lip holder 184-1.

The upper portion of first lip holder 184-1 can be connected to the bottom portion of first lip holder 184-1 via the linear ratcheting mechanism 1006. The first lip holder 184-1 can be height adjustable via the linear ratcheting mechanism 1006.

The linear ratcheting mechanism 1006 can include an adjustment tooth 195 and a plurality of ratcheting teeth 197. The adjustment tooth 195 can engage a particular ratcheting tooth of the plurality of ratcheting teeth 197 to form the linear ratcheting mechanism 1006. For example, adjustment tooth 195 can engage a particular ratcheting tooth such that the upper portion of first lip holder 184-1 and the bottom portion of first lip holder 184-1 are at a fixed height relative to each other, where the fixed height is based on the particular ratcheting tooth of the plurality of ratcheting teeth 197 engaged by the adjustment tooth 195.

The upper portion and bottom portions first lip holder 184-1 can be height adjustable relative to each other by the adjustment tooth 195 engaging a different ratcheting tooth of the plurality of ratcheting teeth 197. For example, the height can be increased or decreased by the adjustment tooth 195 engaging a different particular ratcheting tooth of the plurality of ratcheting teeth 197.

As illustrated in FIG. 1H, the plurality of ratcheting teeth 197 can be angled. Additionally, the adjustment tooth 195 can be angled. The angled plurality of ratcheting teeth 197 and the angled adjustment tooth 195 can allow for the height between the upper portion and the bottom portion to be adjusted to be larger without lifting adjustment tooth 195. For example, the angles of the plurality of ratcheting teeth 197 and the adjustment tooth 195 can be oriented such that the upper portion and the bottom portion can be moved linearly away from each other to increase the height between the upper portion and the bottom portion without lifting adjustment tooth 195. The angles of the plurality of ratcheting teeth 197 and the adjustment tooth 195 can allow the adjustment tooth 195 to slide to different particular ratcheting teeth of the plurality of ratcheting teeth 197 to increase the height.

In an example in which the adjustable cheek retractor is placed in a patient's mouth, allowing the height of the first lip holder 184-1 and/or the second lip holder (e.g., not illustrated in FIG. 1H) of the adjustable cheek retractor to be increased without lifting the adjustment tooth 195 can allow for a user (e.g., the patient, treatment professional, etc.) to increase the height against an opposing force generated by the patient's cheeks and mouth.

The height between the upper portion and the bottom portion can be adjusted to be smaller by pulling adjustment tooth 195 away from the plurality of ratcheting teeth 197 to allow the upper portion to slide towards the bottom portion of first lip holder 184-1. For instance, the angles of the adjustment tooth 195 and the plurality of ratcheting teeth 197 will not allow for movement of the upper portion relative to the bottom portion without pulling adjustment tooth 195 away from the plurality of ratcheting teeth 197. Therefore, a user (e.g., the patient, treatment professional, etc.) can pull adjustment tooth 195 away from the plurality of ratcheting teeth 197 to allow for the upper portion to move linearly towards the bottom portion of first lip holder 184-1 to decrease the height between the upper portion and the bottom portion of first lip holder 184-1. At the desired height between the upper portion and the bottom portion, the user can release the adjustment tooth 195, allowing for the adjustment tooth 195 to engage a particular ratcheting tooth of the plurality of ratcheting teeth 197.

Although not shown in FIG. 1H for clarity and so as not to obscure embodiments of the present disclosure, the second lip holder (e.g., second lip holder 184-2) can include an upper portion, a bottom portion, and a linear ratcheting mechanism. The second lip holder can be height adjustable similar to first lip holder 184-1.

FIG. 2A illustrates a front view of a cheek retractor and a side view of a mobile device holder according to a number of embodiments of the present disclosure. FIG. 2B illustrates a front view of a mobile device holder according to a number of embodiments of the present disclosure. In the embodiments of FIGS. 2A and 2B, the mobile device holder 208 includes an arm 210, an adjustment mechanism 212, and an attachment mechanism 214, where the arm 210 is configured to be attached to cheek retractor 200 (e.g., cheek retractor 100, previously described in connection with FIGS. 1A and 1B), where cheek retractor 200 includes first imaging markers 204-1 and second imaging markers 204-2 (e.g., first imaging markers 104-2 and second imaging markers 104-2, respectively, as previously described in connection with FIGS. 1A and 1B). Mobile device holder 208 further includes a base 216 configured to receive a mobile device 218, a vertical support mechanism 220, an attachment mechanism 222, and adjustable stops 224.

Arm 210 can include adjustment mechanism 212. As used herein, an adjustment mechanism refers to a mechanism allowing arm 210 to be adjusted relative to cheek retractor 200 such that at least one of photographs and video of teeth of the user may be taken by mobile device 218 at different positions relative to cheek retractor 200. In some examples, adjustment mechanism 212 can be a ball joint, although embodiments of the present disclosure are not limited to a ball joint. As used herein, a ball joint refers to a ball-and-socket joint allowing for free movement (e.g., rotation) in various planes. Adjustment mechanism 212 includes attachment mechanism 214. Arm 210 is configured to be attached to cheek retractor 200 via attachment mechanism 214, where cheek retractor 200 is configured to hold a cheek away from a mouth of a user to expose teeth of the user. Attachment mechanism 214 can be a clip, among other types of attachment mechanisms.

Base 216 is attached to arm 210. Base 216 can receive a mobile device 218. As used herein, a mobile device refers to a device including a user interface and a camera capable of taking photographs and/or video. The mobile device can include a camera on a same side of the mobile device as the user interface, and/or a camera on an opposite side of the mobile device of the user interface. As shown in FIGS. 2A and 2B, camera 240 and user interface 242 are on the same side of mobile device 218.

Base 216 can be movable relative to arm 210 such that a distance between mobile device 218 and the teeth of the user is configurable. For example, the base 216 may be slid forward and/or backwards to capture images of the user's teeth that may be required at various distances from the user's teeth, as will be further described herein. Base 216 may slide forward and/or backward on a track. The track may be a slot included in base 216 within which a portion of arm 210 is located, where the track may allow for movement of base 216 relative to arm 210.

The base 216 and/or arm 210 can include soft stops configured to inhibit (e.g., slightly inhibit) movement of base 216 relative to arm 210. As used herein, a soft stop may refer to material included base 216 and/or arm 210 to provide slight resistance to movement of the base 216 relative to arm 210. The soft stops can be located at predetermined locations along the axis of movement of base 216 relative to arm 210, where the predetermined locations can correspond to predefined distances from mobile device 218 to the teeth of the user. As shown in FIG. 2A, base 216 can include distance markings indicating to a user a distance from mobile device 218 to the teeth of the user. The distance markings can include an indicator marking a "correct" distance that may correspond to the distance needed for an image of the user's teeth that may be utilized for case assessment and/or progress tracking.

Mobile device holder 208 can include a vertical support mechanism 220, where the vertical support mechanism 220 includes a vertically adjustable attachment mechanism 222 configured to attach to mobile device 218. Vertically adjustable attachment mechanism 222 can slide up and/or down along an axis of movement defined by vertical support mechanism 220. Attachment mechanism 222 can be vertically adjusted to accommodate differently sized mobile devices 218. For example, attachment mechanism 222 can be slid up vertical support mechanism 220 to accommodate a first mobile device that is taller than a second, shorter mobile device.

Attachment mechanism 222 can prevent vertical movement of mobile device 218. For example, attachment mechanism 222 can prevent mobile device 218 from "tipping" forwards off of base 216.

In some examples, attachment mechanism 222 can be a suction cup. For example, the suction cup can create a vacuum in the suction cup to secure mobile device 218 in order to prevent movement of mobile device 218, such as a "tipping" movement, although embodiments of the present disclosure are not limited to a suction cup as attachment mechanism 222.

As shown in FIG. 2B, base 216 can include adjustable stops 224 configured to prevent lateral movement of mobile device 218. For example, adjustable stops 224 can provide a compressive force on mobile device 218 such that lateral movement (e.g., side-to-side movement) of mobile device 218 is prevented. Adjustable stops 224 can include a cover made of a rubber or other material that may provide friction to assist in preventing lateral movement of mobile device 218.

Adjustable stops 224 can be horizontally adjusted to accommodate differently sized mobile devices 218. For example, adjustable stops 224 can be adjusted sideways to accommodate a first mobile device that is wider than a second mobile device.

Arm 210, adjustment mechanism 212, attachment mechanism 214, base 216, vertical support mechanism 220, and adjustable stops 224 may be a plastic material or other polymer. Arm 210, adjustment mechanism 212, attachment mechanism 214, base 216, vertical support mechanism 220, and adjustable stops 224 may be manufactured from a plastic material or other polymer capable of withstanding the weight of mobile device 218. Arm 210, adjustment mechanism 212, attachment mechanism 214, base 216, vertical support mechanism 220, and adjustable stops 224 may be manufactured by downloading a computer-aided design (CAD) virtual model to a rapid prototyping process, such as, for example, a computer-aided manufacturing (CAM) milling, stereolithography, and/or photolithography process, overmolding, injection molding, and/or a rapid prototyping machine or direct fabrication device, such as a SLA or 3D printing machine, among other manufacturing techniques and/or processes.

Arm 210 can swivel about adjustment mechanism 212 such that an angle between mobile device 218 and the teeth of the user is configurable. Correspondingly, base 216, attached to arm 210, can swivel about adjustment mechanism 212. For example, arm 210 may be swiveled about adjustment mechanism 212 to capture images of the user's teeth that may be required at various angles from the user's teeth.

Mobile device 218 can take at least one of photographs and video of the teeth of the user at configurable distances via base 216 and/or configurable angles via adjustment mechanism 212. The photographs and/or video of the teeth can include at least one of the first imaging markers 204-1 and second imaging markers 204-2.

In some examples, user interface 242 of mobile device 218 can instruct a user to take a photograph of the user's teeth via camera 240, where the photograph is to be taken at a specified distance from the user's teeth. The user may adjust base 216 forwards or backwards so that the camera 240 included in mobile device 218 can take the photograph at the specified distance from the user's teeth, where the photograph includes at least one of the first imaging markers 204-1 and second imaging markers 204-2.

In some examples, user interface 242 of mobile device 218 can instruct a user to take a photograph of the user's teeth via camera 240, where the photograph is to be taken at a specified angle from the user's teeth. The user may adjust arm 210, and correspondingly base 216, by swiveling arm 210 about the adjustment mechanism 212 so that the camera 240 included in mobile device 218 can take the photograph at the specified angle from the user's teeth, where the photograph includes at least one of the first imaging markers 204-1 and second imaging markers 204-2.

The instructions to a user to take at least one of photographs and video of the teeth can be visual instructions via user interface 242, and/or can be audio instructions. In some examples, visual instructions can be presented to the user via user interface 242. In some examples, audio instructions can be broadcast to the user via an audio output of the mobile device, such as a speaker. In some examples, a combination of visual instructions via user interface 242 and audio instructions may be presented to the user.

Attaching mobile device holder 208 to cheek retractor 200 can allow a user to quickly and easily take images of the user's teeth at consistent angles and distances. The consistent images can allow for a more accurate model of the patient's teeth to be created, and accordingly a more accurate case assessment and/or more accurate progress tracking of the patient's dental procedure. Further, the mobile device holder 208 can allow the user to take the images of the user's teeth without the need for help from an additional person.

FIG. 3 illustrates a front view of a mobile device holder according to a number of embodiments of the present disclosure. In the embodiment of FIG. 3, the mobile device holder 330 includes a stand 332 and a base guide 336. The stand 332 can include stop mechanism 334. The base guide 336 can include position and angle markings 338-1, 338-2, 338-3 (referred to collectively as position and angle markings 338).

Stand 332 can be configured to receive a mobile device 318 (e.g., mobile device 118, 218, previously described in connection with FIGS. 1 and 2, respectively). Mobile device 318 can include a user interface 342 (e.g., user interface 242, previously described in connection with FIG. 2) and a camera 340 (e.g., camera 240, previously described in connection with FIG. 2) capable of taking photographs and/or video. Stand 332 may be configured such that it is able to be stood upright. For example, stand 332 may be curved or include members to allow stand 332 to be stood upright. Stand 332 can move relative to teeth of a user such that mobile device 318 can capture at least one of photographs and video of the user's teeth at at least one of various distances and angles from the user's teeth.

In some embodiments, stand 332 may be configured such that at least a portion of the stand 332 is folded. For example, a portion of stand 332 may be folded towards the position and angle markings 338 of the table guide 336 such that stand 332 is able to be stood upright.

Stand 332 can include stop mechanism 334. In some embodiments, stop mechanism 334 can be tabs that may be, for example, a portion of stand 332, although embodiments of the present disclosure are not so limited. Stop mechanism 334 can prevent movement of mobile device 318 with respect to stand 332. For example, stop mechanism 334 can prevent vertical movement of mobile device 318, such as a "tipping" movement.

Stand 332 can be a paper material such as cardboard. For example, stand 332 can be cardboard capable of being folded to receive mobile device 318. However, embodiments of the present disclosure are not limited to stand 332 being cardboard. For example, stand 332 can be plastic or any other material capable of being configured to stand upright and to receive mobile device 318.

Base guide 336 may be configured such that at least a portion of the base guide 336 is folded and the guide is configured into the base. The stand 332 may be located on base guide 336.

Base guide 336 can include at least one of different position and angle markings 338. The different position and angle markings 338 can correspond to predefined distances and/or angles indicating to a user a distance and/or an angle, respectively, from mobile device 318 to the teeth of the user.

Although shown in FIG. 3 as including base guide 336, embodiments of the present disclosure are not so limited. For example, stand 332 including mobile device 318 may be utilized without base guide 336 to capture at least one of photographs and video of a user's teeth at at least one of various distances and angles from the user's teeth.

Mobile device 318 is oriented on stand 332 such that camera 340 of mobile device 318 and user interface 342 of mobile device 318 face toward the position and angle markings 338 of base guide 336. Further, camera 340 of mobile device 318 and user interface 342 of mobile device 318 face toward the teeth of the user.

Mobile device 318 can take at least one of photographs and video of teeth of the user at at least one of the different position and angle markings 338 of base guide 336. User interface 342 can instruct a user to take a photograph and/or video of the user's teeth at specified distances and/or angles from the user's teeth. The user may adjust stand 332 using base guide 336 so that camera 340 can take a photograph and/or a video of the user's teeth at the specified distances and/or angles. For example, user interface 342 can instruct the user to take photographs of the user's teeth at an angle specified by position and angle marking 338-1 and 338-3, as well as a photograph directly in front of the user at position and angle marking 338-2, where the photographs include at least one imaging marker (e.g., imaging markers 104, 204, previously described in connection with FIGS. 1 and 2, respectively) included on a cheek retractor (e.g., cheek retractor 100, 200, previously described in connection with FIGS. 1 and 2, respectively). The cheek retractor can be configured to hold a cheek away from a mouth of the user to expose the teeth of the user.

The instructions to a user to take at least one of photographs and video of the teeth can be visual instructions via user interface 342, and/or can be audio instructions. In some examples, visual instructions can be presented to the user via user interface 342. In some examples, audio instructions can be broadcast to the user via an audio output of the mobile device, such as a speaker. In some examples, a combination of visual instructions via user interface 342 and audio instructions may be presented to the user.

Mobile device holder 330 can allow a user to quickly and easily take images of the user's teeth at consistent angles and distances without the need for help from an additional person. Similar to the embodiment described in connection with FIG. 2, the consistent images can allow for a more accurate model of the patient's teeth to be created, and accordingly a more accurate case assessment and/or more accurate progress tracking of the patient's dental procedure. Further, using a cardboard stand and base guide can allow a treatment professional or other entity to send a cost effective mobile device holder to a user that is easy to ship, as well as providing a mobile device holder for the user that is easy to use and can be disassembled for compact storage.

FIG. 4 illustrates a front view of a mobile device holder according to a number of embodiments of the present disclosure. In the embodiment of FIG. 4, the mobile device holder 444 includes a stand 432 (e.g., stand 332, previously described in connection with FIG. 3), a stand attachment 450, and a base guide 436 (e.g., base guide 336, previously described in connection with FIG. 3). The stand 432 can include stop mechanism 434 and a slot 446. The stand attachment 450 can include a tongue 448 and a reflective surface 452. The base guide 436 can include position and angle markings 438-1, 438-2, 438-3 (referred to collectively as position and angle markings 438), (e.g., position and angle markings 338, previously described in connection with FIG. 3).

Similar to the embodiment of FIG. 3, stand 432 may be configured such that it is able to be stood upright. For example, stand 432 may be curved or include members to allow stand 432 to be stood upright. In some examples, a portion of stand 432 may be folded towards the position and angle markings 438 of the base guide 436 such that stand 432 is able to be stood upright. Stand 432 can move relative to teeth of a user such that mobile device 418 can capture at least one of photographs and video of the user's teeth at at least one of various distances and angles from the user's teeth.

Stand 432 can be configured to receive a mobile device 418 (e.g., mobile device 118, 218, 318, previously described in connection with FIGS. 1-3, respectively). Mobile device 418 can include a user interface and a camera 451 capable of taking photographs and/or video.

Stand 432 can include stop mechanism 434. In some embodiments, stop mechanism 434 can be tabs that may be, for example, a portion of stand 432, although embodiments of the present disclosure are not so limited. Stop mechanism 434 can prevent movement of mobile device 418 with respect to stand 432. For example, stop mechanism 434 can prevent vertical movement of mobile device 418, such as a "tipping" movement.

Stand 432 can be a paper material such as cardboard. For example, stand 432 can be cardboard capable of being folded to receive mobile device 418. However, embodiments of the present disclosure are not limited to stand 432 being cardboard. For example, stand 432 can be plastic any other material capable of being configured to stand upright and to receive mobile device 418.

Base guide 436 may be configured such that at least a portion of the base guide 436 is folded and the guide is configured into the base. The stand 432 may be located on base guide 436.

Base guide 436 can include at least one of different position and angle markings 438. The different position and angle markings 438 can correspond to predefined distances and/or angles indicating to a user a distance and/or an angle, respectively, from mobile device 418 to the teeth of the user.

Although shown in FIG. 4 as including base guide 436, embodiments of the present disclosure are not so limited. For example, stand 432 including mobile device 418 may be utilized without base guide 436 to capture at least one of photographs and video of a user's teeth at at least one of various distances and angles from the user's teeth.

Stand 432 includes a slot 446 configured to receive a tongue 448 of stand attachment 450. For example, tongue 448 of stand attachment 450 can be slid into slot 446 of stand 432 such that stand attachment 450 is attached to stand 432.

Stand attachment 450 can be a paper material such as cardboard, among other types of paper materials. For example, stand attachment 450 can be cardboard capable of being folded such that tongue 448 can be slid into slot 446 of stand 432 to attach stand attachment 450 to stand 432.

A portion of stand attachment 450 can include a reflective surface 452. As used herein, a reflective surface refers to a surface from which light in an incoming direction is redirected to an outgoing direction. Reflective surface 452 can allow a user to see a reflection of the user interface of mobile device 418 when looking at reflective surface 452. For example, the user interface of mobile device 418 can instruct the user to take the photographs and/or video of the user's teeth at different positions and angles (as is further described herein with respect to FIG. 6). Reflective surface 452 can assist the user in taking at least one of photographs and video of the user's teeth at the different position and angle markings 438 by reflecting the user interface of mobile device 418 so that the user can position camera 451 in a correct position relative to the user's mouth/teeth for camera 451 to capture the photographs and/or video of the user's teeth at the correct positions and angles. Reflecting the user interface of mobile device 418 may be useful in assisting in capturing the photographs and/or video of teeth of a user who may be hearing impaired. Reflective surface 452 can be a glass material, a reflective metal (e.g., aluminum, etc.), and/or reflective fabric, among other reflective materials.

The instructions to a user to take at least one of photographs and video of the teeth can be visual instructions via user interface reflected off of reflective surface 452, and/or can be audio instructions. In some examples, visual instructions can be presented to the user via a user interface reflected off of reflective surface 452. In some examples, audio instructions can be broadcast to the user via an audio output of the mobile device, such as a speaker. In some examples, a combination of visual instructions via a user interface reflected off of reflective surface 452 and audio instructions may be presented to the user.

Mobile device 418 is oriented on stand 432 such that camera 451 of mobile device 418 faces towards the position and angle markings 438 of base guide 436 and a user interface of mobile device 418 faces away from the position and angle markings 438 of base guide 436. The user interface of mobile device 418 can be reflected off of reflective surface 452 of stand attachment 450.

Mobile device 418 can take at least one of photographs and video of teeth of the user at at least one of the different position and angle markings 438 of base guide 436. User interface can instruct a user, via reflective surface 452, to take a photograph and/or video of the user's teeth at specified distances and/or angles from the user's teeth (e.g., instructions from the user interface are reflected off reflective surface 452). The user may adjust stand 432, including stand attachment 450, using base guide 436 so that camera 451 can take a photograph and/or a video of the user's teeth at the specified distances and/or angles. For example, the user interface can instruct the user to take photographs of the user's teeth at an angle specified by position and angle marking 438-1 and 438-3, as well as a photograph directly in front of the user at position and angle marking 438-2, where the photographs include at least one imaging marker (e.g., imaging markers 104, 204, previously described in connection with FIGS. 1 and 2, respectively) included on a cheek retractor (e.g., cheek retractor 100, 200, previously described in connection with FIGS. 1 and 2, respectively). The cheek retractor can be configured to hold a cheek away from a mouth of the user to expose the teeth of the user.

Figure 5:
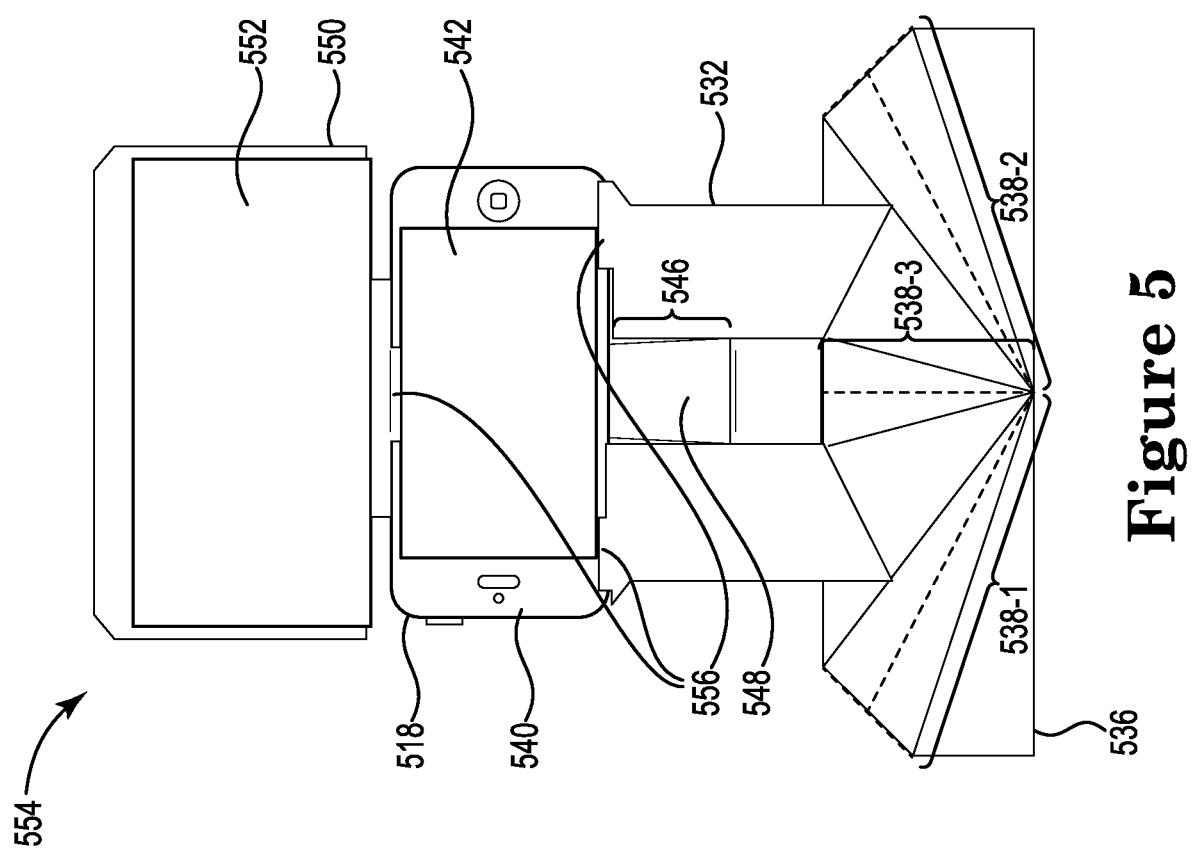
FIG. 5 illustrates a front view of a mobile device holder according to a number of embodiments of the present disclosure.

FIG. 5 illustrates a front view of a mobile device holder according to a number of embodiments of the present disclosure. In the embodiment of FIG. 5, the mobile device holder 554 includes a stand 532 (e.g., stand 332, 432, previously described in connection with FIGS. 3 and 4), a stand attachment 550 (e.g., stand attachment 450, previously described in connection with FIG. 4), and a base guide 536 (e.g., base guide 336, 436, previously described in connection with FIGS. 3 and 4). The stand 532 can include stop mechanism 556 and a slot 546 (e.g., slot 446, previously described in connection with FIG. 4). The stand attachment 550 can include a tongue 548 (e.g., tongue 448, previously described in connection with FIG. 4) and a reflective surface 552 (e.g., reflective surface 452, previously described in connection with FIG. 4). The base guide 536 can include position and angle markings 538-1, 538-2, 538-3 (referred to collectively as position and angle markings 538), (e.g., position and angle markings 338, 438, previously described in connection with FIGS. 3 and 4).

Similar to the embodiment of FIG. 4, stand 532 may be configured such that it is able to be stood upright. For example, stand 532 may be curved or include members to allow stand 532 to be stood upright. In some examples, a portion of stand 532 may be folded towards the position and angle markings 538 of the base guide 536 such that stand 532 is able to be stood upright. Stand 532 can move relative to teeth of a user such that mobile device 518 can capture at least one of photographs and video of the user's teeth at at least one of various distances and angles from the user's teeth.

Stand 532 can be configured to receive a mobile device 518 (e.g., mobile device 118, 218, 318, 418, previously described in connection with FIGS. 1-4, respectively). Mobile device 518 can include a user interface 542 (e.g., user interface 242, 342, previously described in connection with FIGS. 2 and 3) and a camera 540 (e.g., camera 240, 340, previously described in connection with FIGS. 2 and 3) capable of taking photographs and/or video.

Stand 532 can include stop mechanism 556. In some embodiments, stop mechanism 556 can be tabs that may be, for example, a portion of stand 532, although embodiments of the present disclosure are not so limited. Stop mechanism 556 can prevent movement of mobile device 518 with respect to stand 532. For example, stop mechanism 556 can prevent vertical movement of mobile device 518, such as a "tipping" movement.

Stand 532 can be a paper material such as cardboard. For example, stand 532 can be cardboard capable of being folded to receive mobile device 518. However, embodiments of the present disclosure are not limited to stand 532 being cardboard. For example, stand 532 can be plastic any other material capable of being configured to stand upright and to receive mobile device 518.

Base guide 536 is configured such that at least a portion of the base guide 536 is folded and the guide is configured into the base. The stand 532 may be located on base guide 536.

Base guide 536 can include at least one of different position and angle markings 538. The different position and angle markings 538 can correspond to predefined distances and/or angles indicating to a user a distance and/or an angle, respectively, from mobile device 518 to the teeth of the user.

Although shown in FIG. 5 as including base guide 536, embodiments of the present disclosure are not so limited. For example, stand 532 including mobile device 518 may be utilized without base guide 536 to capture at least one of photographs and video of a user's teeth at at least one of various distances and angles from the user's teeth.

Stand 532 includes a slot 546 configured to receive a tongue 548 of stand attachment 550. For example, tongue 548 of stand attachment 550 can be slid into slot 546 of stand 532 such that stand attachment 550 is attached to stand 532.

Stand attachment 550 can be a paper material such as cardboard, among other types of paper materials. For example, stand attachment 550 can be cardboard capable of being folded such that tongue 548 can be slid into slot 546 of stand 532 to attach stand attachment 550 to stand 532.

A portion of stand attachment 550 can include a reflective surface 552. For example, reflective surface 552 can allow a user to see themselves (e.g., their mouth and/or teeth) when looking at reflective surface 552.

Mobile device 518 is oriented on stand 532 such that camera 540 and user interface 542 of mobile device 518 face towards the position and angle markings 538 of base 536. Further, camera 540 of mobile device 518 and user interface 542 of mobile device 518 face toward the teeth of the user.

Mobile device 518 can take at least one of photographs and video of teeth of the user at at least one of the different position and angle markings 538 of base guide 536. User interface 542 can instruct a user to take a photograph and/or video of the user's teeth at specified distances and/or angles from the user's teeth. The user may adjust stand 532, including stand attachment 550, using base guide 536 so that camera 540 can take a photograph and/or a video of the user's teeth at the specified distances and/or angles. For example, the user interface can instruct the user to take photographs of the user's teeth at an angle specified by position and angle marking 538-1 and 538-3, as well as a photograph directly in front of the user at position and angle marking 538-2, where the photographs include at least one imaging marker (e.g., imaging markers 104, 204, previously described in connection with FIGS. 1 and 2, respectively) included on a cheek retractor (e.g., cheek retractor 100, 200, previously described in connection with FIGS. 1 and 2, respectively). The cheek retractor can be configured to hold a cheek away from a mouth of the user to expose the teeth of the user.

The instructions to a user to take at least one of photographs and video of the teeth can be visual instructions via user interface 542, and/or can be audio instructions. In some examples, visual instructions can be presented to the user via user interface 542. In some examples, audio instructions can be broadcast to the user via an audio output of the mobile device, such as a speaker. In some examples, a combination of visual instructions via user interface 542 and audio instructions may be presented to the user. The visual instructions to take at least one of photographs and video of the teeth can be carried out by the user and/or a treatment professional via the mobile device.

Figure 6:
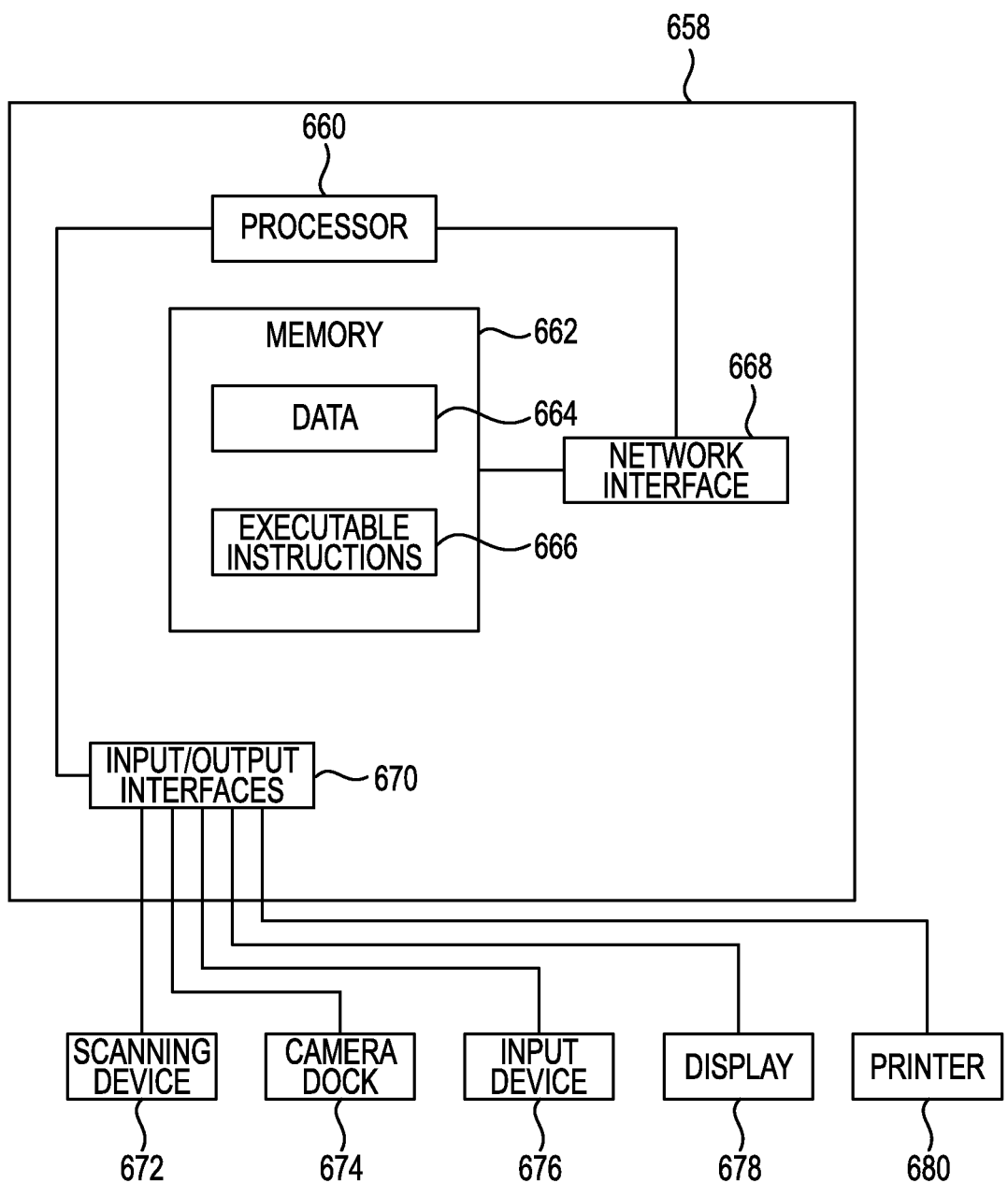
FIG. 6 illustrates a computing device that can be utilized according to one or more embodiments of the present disclosure.

FIG. 6 illustrates a computing device that can be utilized according to one or more embodiments of the present disclosure. For instance, a computing device 658 can have a number of components coupled thereto.

The computing device 658 can include a processor 660 and a memory 662. The memory 662 can have various types of information including data 664 and executable instructions 666, as discussed herein.

The processor 660 can execute instructions 666 that are stored on an internal or external non-transitory computer device readable medium (CRM). A non-transitory CRM, as used herein, can include volatile and/or non-volatile memory.

Volatile memory can include memory that depends upon power to store information, such as various types of dynamic random access memory (DRAM), among others. Non-volatile memory can include memory that does not depend upon power to store information.

Memory 662 and/or the processor 660 may be located on the computing device 658 or off of the computing device 658, in some embodiments. As such, as illustrated in the embodiment of FIG. 6, the computing device 658 can include a network interface 668. Such an interface 668 can allow for processing on another networked computing device, can be used to obtain information about the patient, and/or can be used to obtain data and/or executable instructions for use with various embodiments provided herein.

As illustrated in the embodiment of FIG. 6, the computing device 658 can include one or more input and/or output interfaces 670. Such interfaces 670 can be used to connect the computing device 658 with one or more input and/or output devices 672, 674, 676, 678, 680.

For example, in the embodiment illustrated in FIG. 6, the input and/or output devices can include a scanning device 672, a camera dock 674, an input device 676 (e.g., a mouse, a keyboard, etc.), a display device 678 (e.g., a screen showing a user interface), a printer 680, and/or one or more other input devices. The input/output interfaces 670 can receive executable instructions and/or data, storable in the data storage device (e.g., memory), representing photographs and/or video of teeth of a user.

In some embodiments, computing device 658 can be a mobile device (e.g., mobile device 218, 318, 418, 518, previously described in connection with FIGS. 1-5). The processor 660 can execute instructions 666 to perform a method, including determining whether a mobile device holder (e.g., mobile device holder 208, 330, 444, 554, previously described in connection with FIGS. 2-5, respectively) has positioned the mobile device in a correct orientation with respect to a user's teeth based on an input received by camera 674 of the mobile device. For example, camera 674 can determine whether the mobile device is at the correct length and/or angle with respect to the user's teeth to take an image (e.g., photograph and/or video) of the user's teeth. A cheek of the user can be held away from the mouth of the user to expose the teeth of the user via a cheek retractor (e.g., cheek retractor 100, 200, previously described in connection with FIGS. 1 and 2, respectively) that includes one or more imaging markers (e.g., imaging markers 104, 204, previously described in connection with FIGS. 1 and 2, respectively). The photograph and/or video of the user's teeth include one or more of the imaging markers.

The processor 660 can execute instructions 666 to generate instructions to capture photographs and/or video of teeth of a user. The instructions to capture photographs and/or video of teeth of the user can include preparation instructions with respect to setting up a mobile device holder, such as a mobile device holder 208, 330, 444, and/or 554, previously described in connection with FIGS. 2-5, respectively. The preparation instructions of the mobile device holder can ensure photographs and/or video of the teeth of the user are consistent as dental treatment progresses. The preparation instructions can be carried out by the user and/or a treatment professional.

In some examples, the processor 660 can execute instructions 666 to generate preparation instructions including instructions to attach a mobile device holder (e.g., mobile device holder 208, previously described in connection with FIG. 2) to a cheek retractor (e.g., cheek retractor 100, 200, previously described in connection with FIGS. 1A, 1B, and FIG. 2). In some examples, the processor 660 can execute instructions 666 to generate preparation instructions including instructions to assemble a mobile device holder (e.g., mobile device holder 330, 444, and/or 554, previously described in connection with FIGS. 2-5, respectively), set a table guide on a flat surface in front of the user, and set the assembled mobile device holder on the table guide.

In some examples, the processor 600 can execute instructions 666 to generate preparation instructions including instructions to place the mobile device on the mobile device holder. For example, the instructions can include instructions to place the mobile device on the mobile device holder attached to the cheek retractor or the assembled mobile device holder placed on the flat surface in front of the user.

In some examples, the processor 600 can execute instructions 666 to generate preparation instructions including calibration instructions for the mobile device. For example, the calibration instructions for the mobile device may include generating instructions to move the mobile device holder closer to the user or farther away from the user, and/or to move the mobile device holder to various angles relative to the teeth of the user. In response to the mobile device holder being in a correct position, the processor 600 can execute instructions 666 to generate an indicator that the mobile device holder is in a correct position and generate instructions to mark a position of the mobile device holder at the correct position, including marking a position on the mobile device holder and/or on the table guide. The instructions to move the mobile device can be repeated for different positions and angles such that various correct positions can be marked on the mobile device holder and/or the table guide.

In some examples, the calibration instructions may include instructions to modify flash settings of the mobile device. As used herein, the term "flash settings" can refer to photographic flash, where photographic flash refers to a flash of artificial light to help illuminate a scene during a photograph and/or video capture sequence of a camera (e.g., camera 674) of the mobile device. For example, the instructions to modify flash settings can include instructions to turn a flash on or off, modify an intensity of the flash, a length of the flash, among other flash settings of the mobile device. The flash settings can be modified based on an illumination level of a scene (e.g., illumination of a user's teeth).

In some examples, the processor 600 can execute instructions 666 to generate photograph and/or video capture instructions. The photograph and/or video capture instructions can include instructions to change a position of the mobile device, instructions to take a photograph and/or video f teeth of a user, instructions to take at least one of a number of photographs and video of the user's teeth at a number of different positions, among other photograph and/or video capture instructions, as is further described herein.

The processor 660 can execute instructions 666 to generate an instruction for the mobile device holder to change the position of the mobile device in response to the input indicating the mobile device is in an incorrect position or orientation. For example, if a mobile device is too far away and/or at a wrong angle with respect to a user's teeth, the mobile device is in an incorrect orientation. The mobile device can generate an instruction, including an audio and/or visual instruction to the user, to change the position of the mobile device. The visual instruction can be displayed on a display 678 of the mobile device that includes a user interface.

Generating an instruction for the mobile device holder to change the position of the mobile device can include generating an instruction for the mobile device holder to change a distance from the mobile device to the teeth of the user. For example, if the mobile device is too close to teeth of the user, the mobile device can generate an instruction to inform the user to move the mobile device further away from the teeth. This can be accomplished, for example, by sliding the base (e.g., base 216) of the mobile device holder away from the teeth of the user, as described in connection with FIG. 2, or by moving the stand (e.g., stand 332, 432, 532) of the mobile device holder away from the teeth of the user, as described in connection with FIGS. 3-5. The correct position can correspond to the marked position on the mobile device holder and/or the table guide, as described above.

Generating an instruction for the mobile device holder to change the position of the mobile device can include generating an instruction for the mobile device holder to change an angle of the mobile device with respect to the teeth of the user. For example, if the mobile device is at an incorrect angle with respect to the teeth of the user, the mobile device can generate an instruction to inform the user to change the angle of the mobile device relative to the teeth. This can be accomplished, for example, by swiveling the arm (e.g., arm 210) of the mobile device holder about an adjustment mechanism (e.g., adjustment mechanism 212), as described in connection with FIG. 2, or by moving the stand (e.g., stand 332, 432, 532) to a different angle with respect to the teeth of the user, as described in connection with FIGS. 3-5. The correct position can correspond to the marked position on the mobile device holder and/or the table guide, as described above.

The processor 660 can execute instructions 666 to generate an instruction to take at least one of a photograph and video of the user's teeth in response to the input indicating the mobile device is in a correct orientation. For example, if the mobile device is in the correct orientation for an image of the user's teeth, the mobile device can generate an instruction, including an audio and/or visual instruction to the user, take a photograph and/or a video of the user's teeth.

The processor 660 can execute instructions 666 to generate an instruction to take at least one of a number of photographs and video of the user's teeth at a number of different positions. For example, an instruction can be generated to take eight total photographs of the user's teeth at four different positions, resulting in the user taking two photos at each position (e.g., a specified distance and angle from the teeth of the user). The different positions can correspond to the marked correct positions on the mobile device holder and/or the table guide, as described above.

The processor 660 can execute instructions 666 to generate an instruction to repeat the method until a threshold number of photographs or video are taken at the number of different positions. Continuing with the above example, the threshold number of photographs can be eight photographs. The instruction to take a photograph at the number of different positions can be repeated until the threshold number of photographs at the number of different positions is reached. The threshold number of photographs or video and the number of different positions can be configurable and/or predetermined. For example, the threshold number of photographs can be more or less than eight photographs, and the threshold number of positions can be more or less than four different positions.

In some embodiments, computing device 658 can be a server or other computing device. The processor 660 can execute instructions 666 to receive at least one of photographs and video of teeth of a user. For example, computing device 658 can receive the photographs of the user's teeth as described above (e.g., from a mobile device). Each of the at least one of the photographs and video include imaging markers, where each imaging marker is located a predefined distance from the remaining imaging markers, and where the imaging markers are included on a cheek retractor (e.g., cheek retractor 100, 200, previously described in connection with FIGS. 1 and 2, respectively), configured to hold a cheek away from a mouth of the user to expose the teeth of the user.

The processor 660 can execute instructions 666 to determine a scale for the teeth of the user based on an analysis of at least one of a size of a particular imaging marker or the distance between at least two of the imaging markers included in the at least one of the photographs and video of the teeth of the user. The distance between the imaging markers can be predefined based on the cheek retractor.

Determining the scale for the teeth can include equating the predefined distances between at least two of the imaging markers included in the at least one of the photographs to pixels in the photographs and/or video of the teeth. For example, computing device 658 can utilize the predefined distance between at least two of the imaging markers (e.g., 2.3 cm) to determine the number of pixels between the same imaging markers (e.g., 10 pixels). Based on the analysis, the computing device 658 can determine a number of pixels per cm. Computing device 658 can then determine dimensions of the user's teeth using the scale (e.g., pixels per cm).

The processor 660 can execute instructions 666 to combine photographs of the teeth of the user using the imaging markers as a reference point for consecutive images of the photographs and/or video of the teeth. For example, a user may have an image of the teeth of the user at an angle and an image of the teeth of the user from in front of the user. Computing device 658 can combine the two images using the imaging markers as a common reference point between the two consecutive images.

The processor 660 can execute instructions 666 to generate a scaled model of the teeth of the user using the determined scale for the teeth of the user. For example, the teeth can be scaled and the images of the user's teeth can be combined to generate the scaled model of the teeth. The model can be a 2D model or a 3D model.

The processor 660 can execute instructions 666 to compare the scaled model of the teeth of the user to a predefined model of teeth of the user. The models can be compared for progress tracking of a user's dental procedure. For example, a user may have had a scan of the user's dentition in a beginning stage of the dental procedure. During the procedure, the user takes images of the user's teeth and the scaled model of the teeth is created as the user's dental procedure progresses. The scaled model of the teeth as the user's dental procedure progresses can be compared against the scan of the patient's dentition in the beginning stage of the procedure used to create an ideal model of the patient's dentition during the course of treatment. The comparison can allow a treatment professional to determine whether the user's dental procedure is proceeding as expected, and/or if changes to the dental procedure need to be made.

The embodiments of the present disclosure can provide a number of benefits. For example, the cheek retractor including the imaging markers can assist in generating an accurate model of the user's teeth. The model can allow treatment professionals to determine whether the user's teeth are suitable for a particular dental procedure and/or to track an ongoing dental procedure while the user does not have to travel to the treatment professional's office. Further, utilizing mobile device holders that are consistent with the embodiments of the present disclosure can allow a user to quickly and easily take images of the user's teeth at consistent angles and distances to allow for a more accurate model of the patient's teeth to be created without the need for help from an additional person. The computing device readable medium, devices, and systems described herein can save time and improve the experience of the patient and/or treatment, among other benefits.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A non-transitory computing device readable medium having executable instructions that are executed by a processor to cause a mobile device to perform a method, including:
    determining whether a mobile device holder coupled to a cheek retractor has positioned the mobile device in a correct orientation with respect to a user's teeth based on an input received by a camera of the mobile device;
    generating an instruction for the user to change the position of the mobile device relative to the teeth by changing an angle at which the mobile device holder holds the mobile device relative to the teeth in response to the input; and
    taking at least one of a picture and video of the user's teeth with the mobile device at different positions relative to the teeth as the angle is adjusted;
    wherein:
        a cheek of the user is held away from a mouth of the user to expose the teeth of the user via the cheek retractor.

2. The non-transitory computing device readable medium of claim 1, wherein generating the instruction for the user to change the position of the mobile device includes generating an instruction for the user to change a distance from the mobile device to the user's teeth.

3. The non-transitory computing device readable medium of claim 1, wherein generating the instruction for the user to change the position of the mobile device includes generating the instruction based an indication that the mobile device is in an incorrect position or orientation.

4. The non-transitory computing device readable medium of claim 1, wherein the executable instructions are executed by the processor to cause the mobile device to generate instructions to take at least one of a number of pictures and video of the user's teeth at a number of different positions.

5. The non-transitory computing device readable medium of claim 4, wherein the executable instructions are executed by the processor to cause the mobile device to repeat the method until a threshold number of pictures or video are taken at the number of different positions.

6. The non-transitory computing device readable medium of claim 1, wherein the executable instructions are executed by the processor to cause the mobile device to take one or more pictures of the user's teeth.

7. The non-transitory computing device readable medium of claim 1, wherein the executable instructions are executed by the processor to cause the mobile device to take one or more videos of the user's teeth.

8. The non-transitory computing device readable medium of claim 1, wherein the executable instructions are executed by the processor to cause the mobile device to determine a scale for the user's teeth using one or more markers on the cheek retractor in the at least one of the picture and video.

9. The non-transitory computing device readable medium of claim 8, wherein the executable instructions are executed by the processor to cause the mobile device to determine the scale based on a distance between at least two of the markers and pixels in the at least one of the picture and video.

10. The non-transitory computing device readable medium of claim 8, wherein the executable instructions are executed by the processor to cause the mobile device to determine the scale based on a size of the one or more markers and pixels in the at least one of the picture and video.

11. The non-transitory computing device readable medium of claim 1, wherein the executable instructions are executed by the processor to cause the mobile device to generate a visual instruction, an audible instruction, or a visual instruction and an audible instruction.

12. The non-transitory computing device readable medium of claim 1, wherein generating the instruction includes generating instruction for the user to adjust a position of a first portion of the mobile device holder relative to a second portion of the mobile device holder.

13. The non-transitory computing device readable medium of claim 12, wherein first portion is coupled to the mobile device and is configured to constrain movement of the mobile device relative to the first portion.

14. A method of taking images of a user's teeth, the method comprising:
   determining whether a mobile device holder coupled to a cheek retractor is positioned in a correct orientation with respect to the user's teeth based on an input received by a camera of the mobile device;
   generating an instruction for the user to change the position of the mobile device relative to the teeth by changing an angle at which the mobile device holder holds the mobile device relative to the teeth in response to the input; and
   taking the images of the user's teeth with the mobile device at different positions relative to the teeth as the angle is adjusted, wherein the cheek retractor exposes the user's teeth while taking the images.

15. The method of claim 14, further comprising securing the mobile device to a first portion of the mobile device holder, and attaching the check retractor to a second portion of the mobile device holder.

16. The method of claim 15, wherein the first portion of the mobile device holder is adjustable with respect to the second portion of the mobile device holder.

17. The method of claim 14, further comprising determining a scale for the user's teeth using one or more markers of the cheek retractor in one or more of the images.

18. The method of claim 17, wherein the scale for the user's teeth is based a size of the one or more markers of the cheek retractor in the one or more of the images.

19. The method of claim 17, wherein the scale for the user's teeth is based a distance between markers of the cheek retractor in the one or more of the images.

20. The method of claim 14, wherein the generating the instructions includes generating a visual instruction, an audible instruction, or a visual instruction and an audible instruction.

21. The method of claim 14, further comprising adjusting adjustable stops of the mobile device holder to accommodate a size of the mobile device.

22. A system comprising a non-transitory computing device readable medium having executable instructions that are executed by a processor to cause a mobile device to perform a method, including:
   generating instructions for a user to change a position of the mobile device relative to the user's teeth in response to input from a camera of the mobile device, wherein the instructions include calibration instructions to adjust a distance in which a mobile device holder holds the mobile device relative to the teeth, and wherein the instructions further include imaging angle instructions to change an angle at which the mobile device holder holds the mobile device relative to the teeth to take images of the teeth; and
   taking the images of the user's teeth with the mobile device at different positions relative to the teeth as the angle is adjusted.

23. The system of claim 22, wherein once calibrated, the imaging angle instructions allows controlled movement of the mobile device holder holding the mobile device relative to the teeth.

24. The system of claim 22, further comprising a cheek retractor to expose the user's teeth while taking the images.

25. The system of claim 24, wherein the cheek retractor includes one or more markers for determining a scale for the user's teeth in the images.

26. The system of claim 24, further comprising the mobile device holder attached to the cheek retractor.

27. The system of claim 22, further comprising the mobile device holder, wherein the mobile device holder is configured to accommodate mobile devices having different sizes.

28. The system of claim 22, wherein the executable instructions further comprise instructions to cause the mobile device to generate an indicator that the mobile device holder is in a correct position.

* * * * *